(12) United States Patent
Park et al.

(10) Patent No.: US 10,085,976 B2
(45) Date of Patent: Oct. 2, 2018

(54) PHARMACEUTICAL COMPOSITION FOR PREVENTING OR TREATING NEURODEGENERATIVE DISEASES

(71) Applicant: AJOU UNIVERSITY INDUSTRY-ACADEMIC COOPERATION FOUNDATION, Suwon-si, Gyeonggi-do (KR)

(72) Inventors: Sang Myun Park, Suwon-si (KR); Yu Ree Choi, Suwon-si (KR)

(73) Assignee: AJOU UNIVERSITY INDUSTRY-ACADEMIC COOPERATION FOUNDATION, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/212,054

(22) Filed: Jul. 15, 2016

(65) Prior Publication Data
US 2017/0143686 A1     May 25, 2017

(30) Foreign Application Priority Data

Jul. 15, 2015    (KR) .................. 10-2015-0100430
Jul. 15, 2015    (KR) .................. 10-2015-0100481

(51) Int. Cl.
| | | |
|---|---|---|
| A61K 48/00 | (2006.01) | |
| C07H 21/02 | (2006.01) | |
| C07H 21/04 | (2006.01) | |
| A61K 31/47 | (2006.01) | |
| C12N 15/113 | (2010.01) | |
| G01N 33/68 | (2006.01) | |
| G01N 33/50 | (2006.01) | |

(52) U.S. Cl.
CPC .......... *A61K 31/47* (2013.01); *C12N 15/1137* (2013.01); *C12Y 301/03048* (2013.01); *G01N 33/5058* (2013.01); *G01N 33/6854* (2013.01); *G01N 33/6896* (2013.01); *C12N 2310/14* (2013.01); *C12N 2310/141* (2013.01); *C12N 2310/16* (2013.01); *C12N 2310/531* (2013.01); *G01N 2333/70535* (2013.01); *G01N 2500/10* (2013.01); *G01N 2800/2814* (2013.01); *G01N 2800/2835* (2013.01)

(58) Field of Classification Search
CPC ....................... A61K 31/713; C12N 15/113
See application file for complete search history.

(56) References Cited

PUBLICATIONS

Yu Ree Choi, et al., "Fibrillar α-Synuclein Inhibits Microglial Phagocytosis", Brain Conference 2014, Nov. 6-8, 2014.
Yu Ree Choi and Sang Myun Park, "Fibrillar α-Synuclein Inhibits Microglial Phagocytosis", Ajou Briomedical Conference, Jan. 16-17, 2015, Suwon, Korea.
Yu Ree Choi and Sang Myun Park, "FcγRIIBmediates the inhibitory effect of aggregated α-synuclein on microglial phagocytosis", The 23$^{rd}$ Federation Meeting of Korean Basic Medical Scientists 2015, May 21-22, 2015.
Notice of Allowance dated Feb. 23, 2018 in connection with Korean Patent Application No. 1020150100430.
Kim JH. et al.,"DJ-1 facilities the interaction between STAT1 and its phosphatase, SHP-1, in brain microglia and astrocytes: A novel anti-inflammatory function of DJ-1", Neurobiology of Disease, 60: 1-10, Aug. 20, 2013.
Zhao Jie et al., "Lipopolysacchride-Activated SHP-1-Deficient Motheaten Microglia Release Increased Nitric Oxide, TNF-α, and IL-1β", Glia, 53:304-312, Nov. 1, 2005.
Tanaka T. et al., "Suppression of SHP-1 promotes corticospinal tract sprouting and functional recovery after brain injury", Cell Death and Disease, vol. 4, 1-8, Apr. 4, 2013.
Marsh N. et al., "SHP-1 negatively regulates neuronal survival by functioning as a TrKA phosphatase", Journal of Cell Biology, 163:5, 999-1010, Dec. 8, 2003.
Office Action dated Aug. 1, 2017 in connection with Korean Patent Application No. 10-2016-0089885.
Cao, S. et al. (2010) Fcγ receptors are required for NF-κB signaling, microglial activation and dopaminergic neurodegeneration in an AAV-synuclein mouse model of Parkinson's disease. *Molecular Neurodegeneration* 5:42, pp. 1-12.

*Primary Examiner* — Amy H Bowman
(74) *Attorney, Agent, or Firm* — John P. White; Cooper & Dunham LLP

(57) ABSTRACT

This invention provides a method of treating a neurodegenerative disease selected from the group consisting of Parkinson's disease, dementia with Lewy bodies, and multiple system atrophy, comprising administering a pharmaceutically effective amount of an agent capable of suppressing expression or activity of SHP-1/-2 (Src homology region 2 domain-containing phosphatase-1/-2) or FcγRIIB (IgG Fc receptor II-B) to a subject having the neurodegenerative disease, wherein the agent capable of suppressing expression of SHP-1/-2 or FcγRIIB is selected from the group consisting of miRNA, siRNA, shRNA, antisense oligonucleotide, and a combination thereof capable of specifically binding to mRNA of SHP-1/-2 or FcγRIIB, and the agent capable of suppressing activity of SHP-1/-2 or FcγRIIB is selected from the group consisting of an antibody, an aptamer, an antagonist, and a combination thereof capable of specifically binding to a protein of SHP-1/-2 or FcγRIIB.

1 Claim, 13 Drawing Sheets

Specification includes a Sequence Listing.

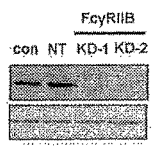
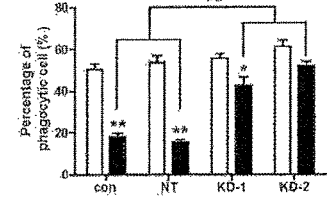
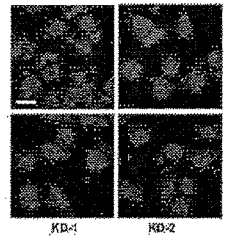
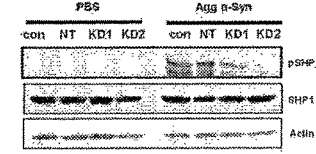
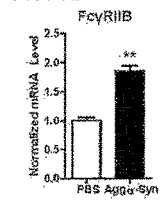
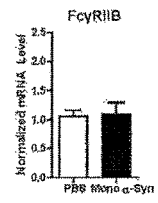
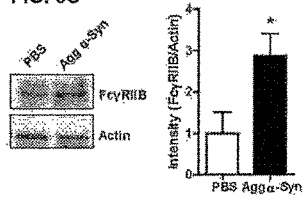
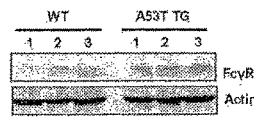
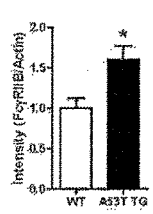
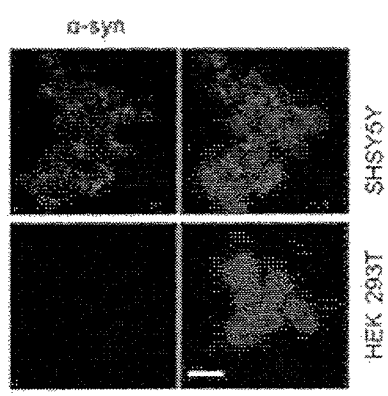
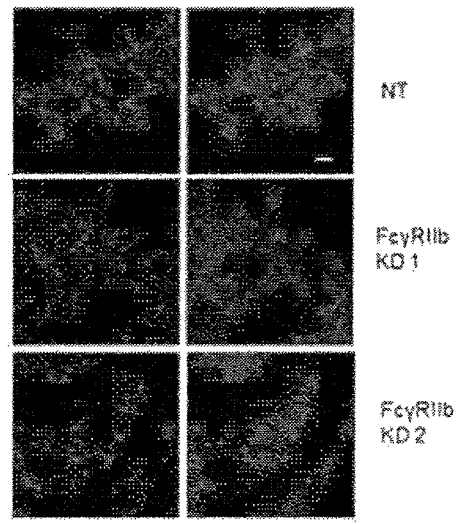

A53T eGFP O/E SH-SY5Y

A53T eGFP O/E SH-SY5Y +
Syn O/E SHSY5Y

A53T eGFP O/E SH-SY5Y +
Syn O/E SHSY5Y + NSC87877

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: forward primer for FcgammaRIIB

<400> SEQUENCE: 1

```
catgtttgag accttcaaca                                              20

<210> SEQ ID NO 2
<211> LENGTH: 20
<212> TYPE: DNA
<213> ORGANISM: Artificial Sequence
<220> FEATURE:
<223> OTHER INFORMATION: reverse primer for FcgammaRIIB

<400> SEQUENCE: 2
gccatctcct gctcgaagtc                                              20

<210> SEQ ID NO 3
<211> LENGTH: 18
<212> TYPE: DNA
<213> ORGANISM: Artificial Sequence
<220> FEATURE:
<223> OTHER INFORMATION: forward primer for actin

<400> SEQUENCE: 3
ggttccagct ctcccagg                                                18

<210> SEQ ID NO 4
<211> LENGTH: 18
<212> TYPE: DNA
<213> ORGANISM: Artificial Sequence
<220> FEATURE:
<223> OTHER INFORMATION: reverse primer for actin

<400> SEQUENCE: 4
ttcatccagg gcttcggg                                                18
```

PHARMACEUTICAL COMPOSITION FOR PREVENTING OR TREATING NEURODEGENERATIVE DISEASES

CROSS-REFERENCE TO RELATED APPLICATIONS

This application claims priority of Korean Patent Applications Nos. KR 10-2015-0100430, filed Jul. 15, 2015 and KR 10-2015-0100481, filed Jul. 15, 2015, the contents of each of which are hereby incorporated by reference into the application.

REFERENCE TO A SEQUENCE LISTING

This application incorporates-by-reference nucleotide and/or amino acid sequences which are present in the file named "161207_88804_Substitute_Sequence_Listing_CAE.txt", which is 1.2 kilobytes in size, and which was created Sep. 19, 2016 in the IBM-PC machine format, having an operating system compatibility with MS-Windows, which is contained in the text file being submitted today.

BACKGROUND OF THE INVENTION

1. Field of the Invention

The present disclosure relates to a pharmaceutical composition for preventing or treating neurodegenerative diseases, and more particularly, the present disclosure relates to a pharmaceutical composition for preventing or treating neurodegenerative diseases including an agent capable of suppressing expression or activity of SHP-1/-2 or FcγRIIB, a method of preventing or treating neurodegenerative diseases by administering the pharmaceutical composition, a method of screening for a therapeutic agent for neurodegenerative diseases, a diagnostic composition for neurodegenerative diseases, a diagnostic kit for neurodegenerative diseases including the diagnostic composition, and a method of diagnosing neurodegenerative diseases using the diagnostic composition or kit.

2. Description of the Related Art

The exact etiology of Parkinson's disease remains unknown, but familial Parkinson's disease is known to be caused by many genetic defects in alpha-synuclein (α-synuclein), parkin, PINK1, DJ-1, LRRK2, etc. Until now, it has been known that oxidative stress, mitochondria disorders, and dysfunction of intracellular protein-clearance mechanism are also considered to cause Parkinson's disease. It is believed that Parkinson's disease is caused by environmental factors as well as genetic factors. Occurrence of Parkinson's disease is diagnosed based on clinical symptoms, and Parkinson's disease is also treated merely by conservative therapy for alleviating symptoms rather than radical therapy. Accordingly, it is urgent to accurately understand the etiology and to find an appropriate therapy corresponding thereto.

Alpha-synuclein (α-synuclein; α-syn) is a major cytoplasmic protein of Lewy body found in patients with Parkinson's disease, and mainly distributed in presynaptic terminals of neurons. Alpha-synuclein is known to be highly expressed throughout the brain tissue. Alpha-synuclein is known to cause other neurodegenerative diseases such as dementia with Lewy bodies, multiple system atrophy, etc. as well as Parkinson's disease. All diseases associated with abnormal accumulation of alpha-synuclein are generally called synucleinopathy, and alpha-synuclein has been actively studied as a common therapeutic target for the diseases.

Further, alpha-synuclein may form aggregates, and it has been suggested that changes of monomeric alpha-synuclein into aggregates may be a main cause of Parkinson's disease. Further, duplication and triplication of alpha-synuclein gene were found in familiar Parkinson's disease, and therefore, many efforts have been actively made to find functions of alpha-synuclein. For example, as a pharmaceutical composition targeting aggregated alpha-synuclein, a pharmaceutical composition for treating Parkinson's disease including Longan Arillus extract as an active ingredient, which is able to significantly protect dopaminergic neurons from neurotoxic effects by alpha-synuclein aggregation, was developed (Korean Patent No. 1189191). However, specific receptors of alpha-synuclein and mechanisms thereof have not been clarified yet.

Meanwhile, change of protein monomers into aggregates occurs in amyloid beta (Aβ) and tau of Alzheimer's disease, mutated huntingtin of Huntington's disease, prion of prion disease, etc., as well as in alpha-synuclein of Parkinson's disease. This change is considered as a common cause of neurodegenerative diseases, and many studies have been actively conducted to treat neurodegenerative diseases by inhibiting the change.

Thereafter, interest in the intracellular delivery of alpha-synuclein is rapidly growing. It is reported that aggregated alpha-synuclein enters neighboring cells to be involved in formation of Lewy bodies and cell death of neighboring cells, like prions in prion disease which bind with normal prions expressed in normal neurons to form aggregates. When pathogenesis of Parkinson's disease by extracellular alpha-synuclein is inferred from the above concept, it is likely that various forms of alpha-synuclein released from cells act on neighboring microglias and activate them to show neuronal toxicity, and furthermore, propagation of alpha-synuclein to neighboring neurons causes direct toxicity or induces formation of Lewy bodies to trigger a series of cytotoxic events.

Therefore, receptors or structures involved in intracellular signaling by extracellular alpha-synuclein may be important clues to elucidate the pathogenesis of many neurodegenerative diseases, and also very interesting in terms of establishing a new therapeutic strategy. However, there have been few studies thereof.

Under this background, the present inventors have made considerable efforts to investigate the mechanism underlying propagation of alpha-synuclein to neighboring cells, and as a result, they found that SHP-1/-2 activation is involved in propagation of alpha-synuclein, and SHP-1/-2 activation is mediated by a receptor for alpha-synuclein, FcγRIIB and therefore, expression or activity of SHP-1/-2 or FcγRIIB is suppressed to inhibit progression of many neurodegenerative diseases caused by alpha-synuclein, thereby completing the present invention.

SUMMARY OF THE INVENTION

An object of the present invention is to provide a pharmaceutical composition for preventing or treating neurodegenerative diseases including an agent capable of suppressing expression or activity of SHP-1/-2 (Src homology region 2 domain-containing phosphatase-1/-2) or FcγRIIB (IgG Fc receptor II-B).

Another object of the present invention is to provide a method of preventing or treating neurodegenerative diseases by administering the pharmaceutical composition.

Still another object of the present invention is to provide a method of screening for a therapeutic agent for neurodegenerative diseases, including the step of measuring whether SHP-1/-2 or FcγRIIB is activated.

Still another object of the present invention is to provide a diagnostic composition for neurodegenerative diseases, including an agent capable of measuring whether SHP-1/-2 or FcγRIIB is activated.

Still another object of the present invention is to provide a diagnostic kit for neurodegenerative diseases, including the diagnostic composition.

Still another object of the present invention is to provide a method of diagnosing neurodegenerative diseases, including the step of measuring whether SHP-1/-2 or FcγRIIB is activated by using the diagnostic composition or kit.

BRIEF DESCRIPTION OF THE DRAWINGS

FIGS. 1A and 1B are the results of BV-2 cells, and FIG. 1D is the result of rat primary microglia. These cells were incubated with indicated doses of aggregated α-syn and fluorescent microspheres for 12 hours, and then phagocytosis assay was performed as described in the following Example 1. In FIG. 1A, blue color indicates DAPI staining, and scale Bar indicates 100 μm.

FIG. 1C is a graph showing the result of LDH-cytotoxicity assay using BV-2 cells which were incubated with 1 μM of aggregated α-syn for 12 hours.

FIGS. 1E and 1F are a graph (FIG. 1E) and electron microscopic images (FIG. 1F) showing the result of Thioflavin T binding assay using aliquots, performed after incubating with 2 mg/ml of monomeric α-syn at 37° C. with agitation at 250 rpm for 2 weeks, and obtaining the small aliquots at indicated time points.

FIGS. 1G and 1H are graphs showing the result of phagocytosis, performed after incubating BV-2 cells with fluorescent microspheres in the presence of 1 μM α-syn at 37° C. with agitation at 250 rpm for indicated times. FIG. 1G is a graph showing the result of incubation for 2 hours, and FIG. 1H shows the result of incubation for 12 hours. * $P<0.05$ and ** $P<0.01$ represent a comparison with the control group.

FIGS. 2A and 2B are graphs showing phagocytic activity in BV-2 cells and in rat primary microglia, respectively. These cells were incubated with indicated doses of aggregated α-syn and 0.5 mg/ml of ICs for 30 minutes, and then incubated with fluorescent microspheres for 2 hours, followed by analysis of phagocytic activity. * $P<0.05$ and ** $P<0.01$ represent a comparison with a non-aggregated α-syn-treated comparison group in the presence of ICs.

FIG. 2C shows an experimental scheme for FIGS. 2D and 2E.

FIGS. 2D and 2E are graphs showing the experimental results in BV-2 cells and in rat primary microglia, respectively. Respective cells were incubated with 0.5 mg/ml of ICs and 1 μM of aggregated α-syn for the indicated times, and then phagocytosis was analyzed. * $P<0.05$ and ** $P<0.01$ represents a comparison with the control group.

FIG. 2F is an image showing the immunostaining result of BV-2 cells. BV-2 cells were pre-incubated with 1 μM of aggregated α-syn for 30 minutes, and then incubated with 0.5 mg/ml of ICs for 10 minutes, followed by cell staining. Under non-permeabilized conditions, the green color indicates ICs immunostained with anti-mouse IgG antibody and the red color indicates α-syn immunostained with anti-α-syn antibody-conjugated Alexa 568.

FIG. 2G is an image showing the immunostaining result of BV-2 cells incubated in the presence or absence of α-syn. The green color indicates ICs immunostained with anti-mouse IgG antibody. After immunostaining, the cells were observed under confocal microscopy, and fluorescence intensity was analyzed. Scale bar indicates 20 μm.

FIGS. 3A and 3B show the experimental results in BV-2 cells and FIG. 3C shows the experimental result in rat primary microglia. These cells were incubated with 1 μM of aggregated α-syn for 30 minutes, and then incubated with 0.5 mg/ml of ICs for 5 minutes.

FIGS. 3D and 3E are graphs and images showing the results of Western blotting of lysates which were obtained after incubating BV-2 cells with 1 μM of monomeric α-syn and 1 μM of aggregated α-syn for 30 minutes, respectively. * $P<0.05$ and ** $P<0.01$ represent a comparison with the control group.

FIG. 3F is image of BV-2 cells and 3G are image of rat primary microglias showing the results of immunostaining, performed after incubating the cells with 1 μM of aggregated α-syn for 5 minutes, respectively. The green color indicates α-syn immunostained with anti-SHP-1 antibody and the red color indicates α-syn immunostained with anti-α-syn antibody. Scale bar indicates 20 μm.

FIG. 3H is an image and a graph showing the results of Western blotting performed by using whole brain lysates of wild-type (WT) and A53T TG mice. * $P<0.05$ represents a comparison with the control WT mouse.

FIG. 4A is an image showing the results of Western blotting for SHP-1 using lysates of a normal comparison group (Non-targeting; NT) and SHP-1 knockdown (KD) BV-2 cells.

FIG. 4B is a graph showing phagocytic activity after incubating the normal comparison group (NT) and SHP-1 knockdown (KD) BV-2 cells with indicated doses of aggregated α-syn and fluorescent microspheres for 12 hours.

FIG. 4C is a graph showing phagocytic activity after pre-incubating the normal comparison group (NT) and SHP-1 knockdown (KD) BV-2 cells with 0.5 mg/ml of ICs for 30 minutes, and then incubating them with 1 μM of aggregated α-syn and fluorescent microspheres for 2 hours.

FIGS. 4D and 4E are graphs showing phagocytic activity after pre-incubating BV-2 cell and rat primary microglia with 20 μM of NSC87877 as an SHP-1 inhibitor for 30 minutes, and then incubating them with 1 NM of aggregated α-syn and fluorescent microspheres for 12 hours. ** $P<0.01$ represents a comparison with the control group.

FIG. 5A is an image showing localization of expressed FcγRIIB, FcγRI and SIRPα in COS-7 cells. COS-7 cells were transfected with myc-tagged FcγRIIB, FcγRI and SIRPα. After incubation for 1 day, the cells were incubated with 1 μM aggregated α-syn for 30 minutes, and then immunostained with anti-myc (green) and anti-α-syn (red) antibodies. The cells were observed under confocal microscopy. Scale bar indicates 20 μm.

FIG. 5B is an image showing the result of co-immunoprecipitation assay performed in order to examine which protein interacts with aggregated α-syn or monomeric α-syn. COS-7 cells were transfected with myc-tagged FcγRIIB and FcγRI, respectively. After incubation for 1 day, the cells were incubated with 1 μM of aggregated α-syn or monomeric α-syn for 30 minutes, and then immunoprecipitation was performed with anti-myc antibody and anti-syn antibody. The asterisks (*) indicate the immunoglobulin G heavy chain.

FIGS. 6A-6H show images and graphs showing that FcγRIIB knockdown rescues the inhibitory effect of aggregated α-syn on microglial phagocytosis.

FIG. 6A is an image showing the results of Western blotting for FcγRIIB using lysates of control group (con), a normal comparison group (non-targeting; NT), and FcγRIIB knockdown (KD) #1 and #2 BV-2 cells.

FIG. 6B is a graph showing the result of analyzing phagocytic activity after incubating the cells with 1 μM of aggregated α-syn and fluorescent microspheres for 12 hours.

FIG. 6C is an image showing the result of immunostaining, performed after incubating the cells with 1 μM of aggregated α-syn for 30 minutes, and fixing and immunostaining the cells with anti-α-syn antibodies (red) under non-permeabilized conditions. The cells were observed under confocal microscopy. Scale bar indicates 20 μm.

FIG. 6D shows graphs and images showing the results of Western blotting of lysates which were obtained after incubating the cells with 1 μM of aggregated α-syn for 5 minutes. ** P<0.01 represents a comparison with PBS and aggregated α-syn.

FIGS. 6E and 6F show graphs showing the results of RT-PCR for the detection of FcγRIIB, performed after incubating BV-2 cells with 1 μM of aggregated α-syn and BV-2 cells with 1 μM of monomeric α-syn for 6 hours, respectively.

FIG. 6G is a graph showing the result of Western blotting, performed after incubating the BV-2 cells with 1 μM of aggregated α-syn for 12 hours. * P<0.05 and ** P<0.01 represent a comparison with PBS.

FIG. 6H is an image and a graph showing the results of Western blotting for the detection of FcγRIIB, performed by using whole brain lysates of wild-type (WT) and A53T TG mice. * P<0.05 represents a comparison with the wild type (WT).

FIGS. 7A-7B show images showing that receptors capable of binding with aggregated α-syn exist on the cell membrane of neurons, and signals are transduced via the receptors.

FIG. 7A is an image of aggregated α-syn in immunostaining, performed after treatment of a human dopaminergic neuronal cell line SH-SY5Y and a human kidney cell line HEK293 cell with aggregated α-syn.

FIG. 7B is an image showing that binding of aggregated α-syn to the plasma membrane of FcγRIIb knockdown SHSY5Y cell was reduced, which is the result of immunostaining using alpha-synuclein antibody after treatment of two FcγRIIb knockdown cell lines (FcγRIIb KD1 and FcγRIIb KD2) with aggregated α-syn for 20 minutes. The red color indicates aggregated α-syn binding to the plasma membrane, and the blue color indicates DNA. Scale bar indicates 20 μm.

FIG. 8A is a graph showing quantification of cytotoxicity of aggregated α-syn to the control undifferentiated SH-SY5Y cells and the differentiated SH-SY5Y cells which were differentiated with retinoic acid for 5 days. ** P<0.01 represents a comparison with the control group.

FIGS. 8B and 8C are an image and a graph showing the effect of FcγRIIb on neurotoxicity of α-syn, and scale bar indicates 20 μm, and an image showing cytotoxicity of aggregated α-syn to differentiated FcγRIIb KD1 and FcγRIIb KD2 cells which were differentiated with retinoic acid for 5 days, and a graph showing quantification of the cytotoxicity. *** P<0.0001 represents a comparison with the normal comparison group (NT).

FIG. 9A is an image of Western blot for measuring FcγRIIb expression levels in FcγRIIb knockdown SHSY5Y cells. α-syn-overexpressed SH-SY5Y cells and FcγRIIb knockdown SH-SY5Y cells were cultured using a two-chamber system for 12 hours. Thereafter, to investigate translocation of α-syn released from SH-SY5Y cells into FcγRIIb knockdown SH-SY5Y cells, alpha-synuclein antibody was used to perform immunostaining.

FIGS. 9B and 9C show images and graphs showing the results of immunostaining. Scale bar indicates 20 μm, and *** P<0.0001 represents a comparison with the normal comparison group (NT). The red color indicates propagated α-syn, and the blue color indicates DNA. NT indicates a non-targeting control SH-SY5Y cell, and FcγRIIb KD1 and FcγRIIb KD2 indicate FcγRIIb knockdown SH-SY5Y cells.

FIGS. 9D and 9E show images and graphs showing the results of immunostaining performed to further investigate the above results. Cos7 cells were transfected with myc-tagged human FcγRIIb (hFcγRIIb), followed by incubation for one day, and the cells were co-cultured with α-syn-overexpressed SHSY5Y cells using a two-chamber system for 12 hours. Thereafter, to investigate translocation of α-syn released from SHSY5Y into the tagged human FcγRIIb (hFcγRIIb)-transfected cos7 cells, anti-alpha-synuclein antibody (red) and anti-myc antibody (green) were used to perform immunostaining. Scale bar indicates 20 μm, and * P<0.05 and *** P<0.0001 represent a comparison with the myc (green)-free cells. The red color indicates propagated α-syn, the green color indicates myc-tagged transfected receptors, and the blue color indicates DNA.

FIGS. 9F and 9G show images and graphs showing that FcγRIIb affects α-syn propagation by ICs. Immune complex-treated SHSY5Y cells were co-cultured with α-syn-overexpressed SHSY5Y cells using a two-chamber system for 12 hours. In order to investigate entrance of α-syn into SHSY5Y cells, immunostaining was performed using anti-α-syn. Next, an image and a graph analyzed by confocal microscopy are shown. Scale bar indicates 20 μm, and *** P<0.0001 represents a comparison with the PBS-treated group. The red color indicates propagated α-syn, and the blue color indicates DNA.

FIGS. 10A and 10D are images and graphs showing that α-syn propagation was reduced in SHP-1 knockdown BV2. Scale bar indicates 20 μm, and *** P<0.001 represents a comparison with the control group.

FIGS. 10N and 10P are images and graphs showing that propagation of α-syn is reduced in OLN 93 cell line treated with the SHP-1,2 inhibitor NSC87877. *** P<0.001 represents a comparison with the PBS-treated group.

FIG. 11A is an image showing the result of immunostaining of aggregated α-syn, after treating a human dopaminergic neuronal cell line, SH-SY5Y and a human kidney cell line, HEK293 cell with aggregated α-syn. Scale bar indicates 20 μm. The red color indicates α-syn, and the blue color indicates DNA.

FIG. 11B is an image showing the result of Western blot to investigate SHP-1 phosphorylation levels by aggregated α-syn in the human dopaminergic neuronal cell line, SH-SY5Y.

FIG. 11C is an image showing that SHP-1 and SHP-2 phosphorylations are increased by aggregated α-syn in rat nerve cells.

FIG. 11D is an image showing that SHP-1/2 phosphorylations were increased by aggregated α-syn in differentiated SHSY5Y and undifferentiated SHSY5Y cell lines.

FIGS. 11E and 11F are images and graphs showing that SHP-2 phosphorylation is also increased in the whole brain lysates of A53T α-syn TG mice. *** P<0.001 represents a comparison with the wild type (WT) mice.

FIG. 12A shows an image showing cytotoxicity of aggregated α-syn on control undifferentiated SH-SY5Y cells and differentiated SH-SY5Y cells which were differentiated with retinoic acid for 5 days, and a graph showing quantification of the cytotoxicity.

FIG. 12B is a graph showing the effect of the SHP-1/2 inhibitor, NSC87877 on cytotoxicity of aggregated α-syn in undifferentiated SH-SY5Y cells and differentiated SH-SY5Y cells.

FIGS. 12C and 12D are images and graphs showing the effect of the SHP-1/2 inhibitor, NSC87877 on cytotoxicity of aggregated α-syn in differentiated SH-SY5Y cells. ** P<0.01 represents a comparison with the PBS-treated SHSY5Y.

FIGS. 12E and 12F are images and graphs showing cytotoxicity of aggregated α-syn in differentiated SHP-1 knockdown SH-SY5Y cells. Scale bar indicates 100 μm, and ** P<0.01 represents a comparison with NT SHSY5Y.

FIG. 14A is an image of confocal microscopy after differentiation of only A53Tα-syn-overexpressed SHSY5Y cells with retinoic acid for 5 days.

FIG. 14B is an image of confocal microscopy after differentiation with retinoic acid for 5 days in the co-culture of A53Tα-syn-overexpressed SHSY5Y and α-syn-overexpressed SHSY5Y cell.

FIG. 14C is an image of confocal microscopy after differentiation with retinoic acid for 5 days in the co-culture of A53Tα-syn-overexpressed SHSY5Y and α-syn-overexpressed SHSY5Y under treatment of the SHP-1/2 inhibitor, NSC87877. Scale bar indicates 20 μm.

DETAILED DESCRIPTION OF THE PREFERRED EMBODIMENTS

Figure 1A:
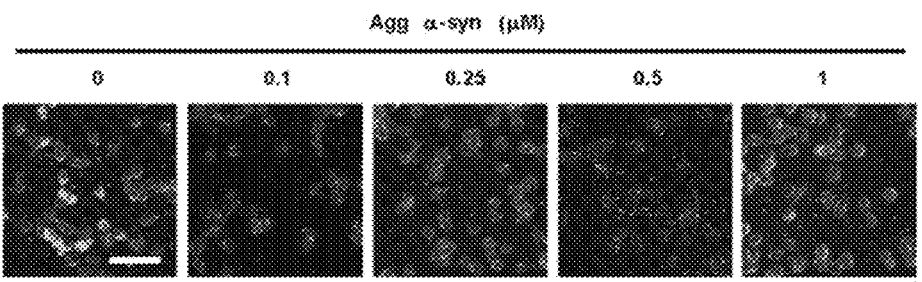
FIGS. 1A-1H show images and graphs showing that aggregated α-synuclein (α-Syn) inhibited microglial phagocytosis.
Figure 1B:
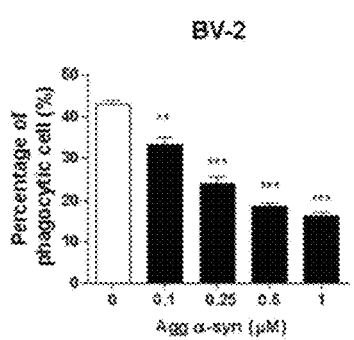

The present inventors demonstrated the pathogenesis of neurodegenerative diseases and conducted many studies to establish a more effective new therapeutic strategy, and as a result, they have focused on alpha-synuclein (α-synuclein; α-syn). Based on the concept that alpha-synuclein released from neurons act on neighboring microglias and activate them to be involved in neuronal damage, they revealed a receptor mediating propagation of extracellular aggregated alpha-synuclein to neighboring cells and a protein activated by the receptor.

The present inventors demonstrated that aggregated α-syn inhibits microglial phagocytosis, and took advantage of immune complex (ICs)-induced phagocytosis to explore the mechanism of action of aggregated α-syn. Further, the present inventors investigated that ICs-involved FcγRs signaling pathways are inhibited by the recruitment of several phosphatases such as SHP-1 and SHP-2 (hereinafter, referred to as SHP-1/-2), and therefore, they examined the effect of aggregated α-syn on SHP-1/-2 activation. As a result, they found that aggregated α-syn induces the translocation of activated SHP-1 to the plasma membrane to inhibit the early stage of ICs-FcγRs which is a signaling pathway of phagocytosis, and SHP-1/-2 activation by aggregated α-syn is mediated by FcγRIIB receptors on microglia.

Furthermore, it was confirmed that α-syn propagation was decreased in SHP-1/-2 knockdown microglia and a normal dopaminergic neuronal cell line SH-SY5Y treated with a SHP-1/-2 inhibitor NSC87877, and SHP-2 phosphorylation was increased in a human kidney cell line where receptor proteins including FcγRIIB are overexpressed. Therefore, it can be seen that SHP-1/-2 activation by phosphorylation is an important factor in the propagation of aggregated α-syn, and the aggregated α-syn transduces signals into cells via FcγRIIb receptors expressed in neurons. It was also confirmed that α-syn propagation was decreased in the FcγRIIb knockdown dopaminergic neuronal cell line SH-SY5Y, suggesting that FcγRIIb is involved in the propagation of α-syn released from different cells to neighboring cells.

The mechanism underlying propagation of aggregated α-syn to neighboring cells which is an important clue to elucidate the pathogenesis of many neurodegenerative diseases has not been disclosed and has been first demonstrated by the present inventors.

In an aspect to achieve the above descried objects, the present invention provides a pharmaceutical composition for preventing or treating a neurodegenerative disease selected from the group consisting of Parkinson's disease, dementia with Lewy bodies, and multiple system atrophy, including an agent capable of suppressing expression or activity of SHP-1/-2 (Src homology region 2 domain-containing phosphatase-1/-2) or FcγRIIB (IgG Fc receptor II-B; FcgammaRIIB)

As used herein, the term "FcγRIIB" refers to a kind of IgG Fc receptor (FcγRs), and with respect to the objects of the present invention, FcγRIIB may be a receptor protein which is considered to be involved in SHP-1/-2 activation by aggregated alpha-synuclein. A nucleotide sequence of the FcγRIIB protein may be obtained from a known database, such as GenBank of NCBI, etc., and for example, a gene represented by GenBank Accession AAA97464.1, etc.

As used herein, the term "FcγRs (IgG Fc receptor)", a regulator of cell activation humoral tolerance, refers to a receptor involved in the regulation of both the afferent and efferent phases of immune response. FcγRs functions as a critical effector of the acute inflammatory response to immune complexes (ICs)

As used herein, the term "FcγRIIB activity" refers to triggering of intracellular signal transduction through binding of FcγRIIB receptors with ligands, and a specific example of the ligand may be aggregated α-syn. With respect to the objects of the present invention, inhibition of the FcγRIIB activity may be achieved by interfering with binding of FcγRIIB to aggregated α-syn as the ligand. Specific examples may include modification of the receptor structure, use of receptor antagonists, etc., but are not limited thereto.

As used herein, the term "alpha-synuclein (α-synuclein; α-syn)" refers to a protein known as a major cytoplasmic protein of Lewy body, but is not limited to, a protein molecule involved in the pathogenesis of neurodegenerative diseases, with respect to the objects of the present invention. A nucleotide sequence of the α-syn gene may be obtained from the known database, such as GenBank of NCBI, etc., and for example, a gene represented by GenBank Accession NP_001035916.1, etc.

As used herein, the term "propagation of alpha-synuclein" refers to translocation of alpha-synuclein from cells releasing alpha-synuclein to different neighboring cells, but is not limited to, a phenomenon of being directly toxic to neighboring cells or a phenomenon of transducing cytotoxic signals into neighboring cells, with respect to the objects of the present invention. The propagation of alpha-synuclein may cause SHP-1/-2 activation.

As used herein, the term "SHP-1/-2", Src homology region 2 domain-containing phosphatase-1/-2, also known as PTPN6 (Tyrosine-protein phosphatase non-receptor type 6), refers to a kind of protein tyrosine phosphatase. The SHP-1/-2 includes a Src homolog (SH2) domain at the N-terminal, the SH2 domain acting as a protein phosphorylation-tyrosine binding domain. The SHP-1/-2 are known as signaling molecules that regulate a variety of cellular processes including cell growth, differentiation, mitotic cycle, etc. With respect to the objects of the present invention, SHP-1/-2 may be proteins activated by aggregated α-syn. Nucleotide sequences of the SHP-1/-2 proteins may be obtained from the known database, such as GenBank of NCBI, etc., and for example, genes represented by GenBank Accession AAC36009.1 and AAC36008.1.

As used herein, the term "SHP-1/-2 activation" refers to SHP-1/-2 phosphorylation, and with respect to the objects of the present invention, the SHP-1/-2 activation may be achieved by aggregated α-syn, and involved in a phenomenon of increasing propagation of α-syn to different neighboring cells.

As used herein, the term "agent capable of suppressing expression or activity of FcγRIIB" refers to a substance capable of suppressing expression or activity of FcγRIIB by directly or indirectly binding to FcγRIIB-encoding gene, mRNA or protein. In the present invention, the agent capable of suppressing expression or activity of FcγRIIB may be used interchangeably with an FcγRIIB inhibitor.

With respect to the objects of the present invention, the agent capable of suppressing expression or activity of FcγRIIB may be an active ingredient of the pharmaceutical composition which suppresses expression or activity of FcγRIIB to exhibit a prophylactic or therapeutic effect on neurodegenerative diseases, and specific examples of the agent may be, but are not particularly limited to, miRNA, siRNA, shRNA, or antisense oligonucleotide specific to FcγRIIB mRNA, or an antibody, an aptamer, an antagonist, etc. capable of specifically binding to FcγRIIB protein.

As used herein, the term "agent capable of suppressing expression or activity of SHP-1/-2" refers to a substance capable of suppressing expression or activity of SHP-1/-2 by directly or indirectly binding to SHP-1/-2-encoding genes, mRNAs or proteins. In the present invention, the agent capable of suppressing expression or activity of SHP-1/-2 may be used interchangeably with an SHP-1/-2 inhibitor.

With respect to the objects of the present invention, the agent capable of suppressing expression or activity of SHP-1/-2 may be an active ingredient of the pharmaceutical composition which suppresses expression or activity of SHP-1/-2 to exhibit a prophylactic or therapeutic effect on neurodegenerative diseases, and specific examples of the agent may be, but are not particularly limited to, miRNAs, siRNAs, shRNAs, or antisense oligonucleotides specific to SHP-1/-2 mRNAs, or antibodies, aptamers, antagonists, etc. capable of specifically binding to SHP-1/-2 proteins.

As used herein, the term "miRNA, siRNA or shRNA" refers to a nucleic acid molecule that mainly binds to mRNA transcribed from a target gene, thereby suppressing mRNA translation in order to mediate RNA interference or gene silencing. Since the siRNA or shRNA is able to suppress expression of the target gene at a translational level, it may be used in efficient gene knockdown or gene therapy method. With respect to the objects of the present invention, the siRNA or shRNA may be used to suppress expression of SHP-1/-2 or FcγRIIB.

As used herein, the term "antisense oligonucleotide" refers to DNA, RNA, or a derivative thereof containing a nucleotide sequence complementary to a particular mRNA sequence, and binds to a complementary sequence in mRNA to suppress translation of mRNA to protein. With respect to the objects of the present invention, the antisense oligonucleotide may be used to suppress expression of SHP-1/-2 or FcγRIIB.

As used herein, the term "antibody" refers to a protein molecule specifically binding to an epitope of a protein or peptide molecule. To prepare the antibody, each gene is cloned into an expression vector according to a common method to obtain a protein encoded by the marker gene, and then the antibody may be prepared from the obtained protein according to a common method.

With respect to the objects of the present invention, the antibody is interpreted as a means that binds to activated SHP-1/-2 or FcγRIIB protein of a subject suspected of having neurodegenerative diseases to inhibit activity of the protein. Specific examples thereof may include a polyclonal antibody, a monoclonal antibody, or a part thereof having antigen-binding property, which is able to specifically bind to SHP-1/-2 or FcγRIIB. Further, all classes of immunoglobulin antibodies may be included, and special antibodies, such as humanized antibodies, may be also included. Furthermore, the antibody may include complete forms having two full-length light chains and two full-length heavy chains, as well as functional fragments of antibody molecules. The functional fragments of antibody molecules refer to fragments retaining at least an antigen-binding function, and may include Fab, F(ab'), F(ab')$_2$, Fv or the like.

As used herein, the term "aptamer" refers to a nucleic acid molecule having a binding affinity for a predetermined target molecule. The aptamer may be an RNA, a DNA, a modified nucleic acid or a mixture thereof, which can also be in a linear or circular form. In general, it is known that as the aptamer is composed of a shorter nucleotide sequence, its chemical synthesis and mass-production are easier, there is an advantage in terms of cost, its chemical modification is easy, in-vivo stability is excellent, and toxicity is low.

With respect to the objects of the present invention, the aptamer is interpreted as a means that binds to SHP-1/-2 or FcγRIIB protein to inhibit activity of the protein.

As used herein, the term "antagonist" refers to a molecule capable of directly or indirectly reducing biological activity of a receptor, and includes a molecule capable of reducing action of the ligand, when used together with the ligand of the receptor, but is not limited thereto.

With respect to the objects of the present invention, the antagonist includes any molecule without limitation, as long as the molecule inhibits activity of the SHP-1/-2 or FcγRIIB protein. A specific example of the antagonist means a molecule that binds to SHP-1/-2 or FcγRIIB to inhibit activity thereof, but is not limited thereto.

Further, the antagonist inhibits activity of SHP-1/-2 or FcγRIIB protein by aggregated α-syn, and therefore, it may be used as a therapeutic agent for all diseases associated with alpha-synuclein, and specifically, as a therapeutic agent for neurodegenerative diseases.

As used herein, the term "neurodegenerative diseases" refer to brain diseases caused by neuronal damage. It is considered that neurodegenerative diseases are caused by aging, genetic mutations, stress, dysfunction of intracellular protein-clearance mechanism, etc., but the exact etiology has not been clarified. The neurodegenerative diseases are not particularly limited, as long as they belong to neurodegenerative diseases caused by alpha-synuclein. Examples thereof may include Parkinson's disease, dementia with Lewy bodies, multiple system atrophy, etc.

As used herein, the term "prevention" refers to all of the actions by which occurrence of neurodegenerative diseases is restrained or retarded by administration of the pharmaceutical composition including the agent capable of suppressing expression or activity of FcγRIIB of the present invention as an active ingredient.

As used herein, the term "treatment" refers to all of the actions by which the symptoms of a subject having or being suspected of having neurodegenerative diseases have taken a turn for the better or been modified favorably by administration of the pharmaceutical composition.

The pharmaceutical composition of the present invention may be prepared as a pharmaceutical composition for treating neurodegenerative diseases, further including an appropriate carrier, excipient, or diluent which is commonly used in the preparation of pharmaceutical compositions. The carrier may include a non-naturally occurring carrier. Specifically, the pharmaceutical composition may be formulated into formulations for oral administration, such as a powder, a granule, a tablet, a capsule, a suspension, an emulsion, a syrup, an aerosol, etc., or as formulation for external application, suppository, and sterile injectable solution, according to common methods.

Specific examples of the carrier, excipient or diluent that may be included in the pharmaceutical composition of the present invention may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc.

During formulation, a commonly used diluent or excipient such as a filler, an extender, a binder, a wetting agent, a disintegrant, a surfactant, etc. may be used for formulation.

Solid formulations for oral administration may include a tablet, a pill, a powder, a granule, a capsule, or the like. The solid formulation may be prepared by mixing with at least one excipient, e.g., starch, calcium carbonate, sucrose, lactose, gelatin, etc. Also, a lubricant such as magnesium stearate or talc may be used, in addition to the simple excipients.

Liquid formulations for oral administration may include a suspension, a solution for internal use, an emulsion, a syrup, or the like. In addition to commonly used simple diluents such as water and liquid paraffin, various excipients, e.g., a wetting agent, a sweetener, an aromatic, a preservative, etc., may be included.

Formulations for parenteral administration may include a sterilized aqueous solution, a non-aqueous solution, a suspension, an emulsion, a freeze-dried preparation, suppository, etc. The non-aqueous solution or suspension may include propylene glycol, polyethylene glycol, vegetable oil such as olive oil, injectable ester such as ethyl oleate, etc.

As a base for the suppository, witepsol, macrogol, tween 61, cocoa butter, laurin butter, glycerogelatin, etc. may be used.

A content of the agent capable of suppressing expression or activity of SHP-1/-2 or FcγRIIB in the pharmaceutical composition of the present invention is not particularly limited, but the agent may be included in an amount of 0.0001 to 50% by weight, and more specifically, 0.01 to 20% by weight, based on the total weight of the final composition.

The pharmaceutical composition of the present invention may be administered in a pharmaceutically effective amount, and as used herein, the term "pharmaceutically effective amount" refers to an amount sufficient to treat or prevent diseases, at a reasonable benefit/risk ratio applicable to any medical treatment or prevention. The effective dosage level may be determined depending on severity of the disease, activity of the drug, a patient's age, body weight, health and sex, sensitivity to the drug, administration time, administration route, and excretion rate of the composition of the present invention, duration of treatment, drugs used simultaneously or in combination with the composition of the present invention, and other factors known in the medical field. The pharmaceutical composition of the present invention may be administered alone or in combination with the known immunotherapeutic agents. It is important to administer the composition in the minimum amount that may exhibit the maximum effect without causing side effects, in view of all the above-described factors.

The administration dose of the pharmaceutical composition of the present invention may be determined by those skilled in the art, considering purpose of use, severity of disease, a patient's age, body weight, sex, history, a kind of a substance used as an active ingredient, etc. For example, the pharmaceutical composition of the present invention may be administered at a dosage of about 0.1 ng/kg to about 100 mg/kg, specifically, about 1 ng/kg to about 10 mg/kg per adult, and the administration frequency of the composition of the present invention may be, but is not particularly limited to, either only once or in divided doses a day. The administration does not limit the scope of the present invention in all aspects.

In another aspect, the present invention provides a method of preventing or treating neurodegenerative diseases, including the step of administering a pharmaceutically effective amount of the pharmaceutical composition to a subject.

As used herein, the term "subject" may include mammals including mice, livestock, humans, etc., farmed fish, etc., who are suspected of having or already have neurodegenerative diseases, without limitation.

The pharmaceutical composition for preventing or treating neurodegenerative diseases of the present invention may be administered via any of the common routes, as long as it is able to reach a desired tissue. The pharmaceutical composition of the present invention may be administered, but is not particularly limited to, intraperitoneally, intravenously, intramuscularly, subcutaneously, intradermally, orally, intranasally, intrapulmonarily or intrarectally according to the desired purpose. However, since the agent capable of suppressing expression or activity of SHP-1/-2 or FcγRIIB may be denatured by gastric acid upon oral administration, active ingredients of a composition for oral administration may be coated or formulated for protection against degradation in the stomach. In addition, the composition may be administered using a certain apparatus capable of transporting the active ingredients into a target cell.

In still another aspect, the present invention provides a method of screening for a therapeutic agent for neurodegenerative diseases, including the steps of treating alpha-synuclein (α-Synuclein) to nerve tissue-derived cells which are treated with a candidate therapeutic agent for a neurodegenerative disease selected from the group consisting of Parkinson's disease, dementia with Lewy bodies, and multiple system atrophy, and then measuring whether SHP-1/-2 or FcγRIIB is activated.

For example, the screening method may include the steps of (a) treating alpha-synuclein (α-Synuclein) to nerve tissue-derived cells which are treated with a candidate therapeutic agent for a neurodegenerative disease; and (b) measuring whether SHP-1/-2 or FcγRIIB is activated in the nerve tissue-derived cells which are administered with the candidate.

As used herein, the term "SHP-1/-2 activation" is the same as described above, and "whether SHP-1/-2 is activated" means whether SHP-1/-2 is phosphorylated.

As used herein, the term "FcγRIIB activation" means binding of aggregated alpha-synuclein to FcγRIIB, and "whether FcγRIIB is activated" means whether FcγRIIB binds with aggregated α-syn.

The screening method may include the step of determining the candidate treated in step (a) as a therapeutic agent for neurodegenerative diseases when the activation of SHP-1/-2 or FcγRIIB measured in step (b) is suppressed.

In the step of (b) measuring whether SHP-1/-2 or FcγRIIB is activated in the nerve tissue-derived cells which are administered with alpha-synuclein (α-Synuclein) and the candidate, a method of measuring expression levels commonly used in the art as described above may be used without limitation, but is not limited to, specifically exemplified by Western blot, co-immunoprecipitation assay, ELISA (Enzyme Linked Immunosorbent Assay), real-time RT-PCR, electrophoresis, immunostaining, FACS (Fluorescence activated cell sorter), etc.

Further, the nerve tissue-derived cells which are treated with the candidate therapeutic agent for neurodegenerative diseases may be, but are not limited to, exemplified by neurons or neuroglias, and other examples thereof may be neuroglias such as microglias, astrocytes, oligodendrocytes, ependymal cells, Schwann cells, satellite cells, etc.

As used herein, the term "candidate therapeutic agent for neurodegenerative diseases" refers to a substance expected to treat neurodegenerative diseases, and any substance may be used without limitation, as long as it is expected to directly or indirectly take a turn for the better or improve neurodegenerative diseases. The candidate includes all substances which are expected to treat the diseases, such as compounds, genes, proteins, etc.

The screening method of the present invention may be used to measure whether the SHP-1/-2 or FcγRIIB is activated before and after administration of the candidate, and to determine the candidate as a therapeutic agent for neurodegenerative diseases when the SHP-1/-2 or FcγRIIB activation is suppressed after administration of the corresponding candidate, compared to before administration thereof.

In still another aspect, the present invention provides a diagnostic composition for a neurodegenerative disease selected from the group consisting of Parkinson's disease, dementia with Lewy bodies, and multiple system atrophy, including the agent capable of measuring whether SHP-1/-2 or FcγRIIB is activated.

As used herein, the term "agent capable of measuring whether SHP-1/-2 is activated" refers to an agent capable of measuring whether SHP-1/-2 is phosphorylated, and with respect to the objects of the present invention, the agent refers to an agent which may be used in the evaluation of the effects of aggregated α-syn on cells. Specific examples of the agent may be, but are not particularly limited to, an antibody or an aptamer capable of specifically binding to activated SHP-1/-2 protein.

As used herein, the term "agent capable of measuring whether FcγRIIB is activated" refers to an agent capable of measuring whether FcγRIIB binds to aggregated α-syn, and with respect to the objects of the present invention, the agent refers to an agent which may be used in the evaluation of the effects of aggregated α-syn on cells. Specific examples of the agent may be, but are not particularly limited to, an antibody or an aptamer capable of specifically binding to FcγRIIB protein.

As used herein, the term "diagnosis" refers to confirmation of a pathological state or characteristic. With respect to the objects of the present invention, the diagnosis is to confirm the incidence of neurodegenerative diseases as well as to determine prognosis such as recurrence following treatment of neurodegenerative diseases, metastatic spread, drug reactivity, resistance, etc.

As used herein, the term "subject" refers to any animal (e.g., a human), and includes horses, dogs, cats, pigs, goats, rabbits, hamsters, monkeys, guinea pigs, rats, mice, lizards, snakes, sheep, cattle, fish, and birds without limitation. More broadly, the subject may include cell lines of the animals without limitation.

In still another aspect, the present invention provides a diagnostic kit for a neurodegenerative disease selected from the group consisting of Parkinson's disease, dementia with Lewy bodies, and multiple system atrophy, including the diagnostic composition.

The diagnostic kit for neurodegenerative diseases of the present invention may include a primer or a probe for directly detecting the propagation of alpha-synuclein (α-Synuclein) as a diagnostic marker of neurodegenerative diseases to neighboring cells, or for measuring activity of SHP-1/-2 or FcγRIIB activated by binding of alpha-synuclein, or an antibody selectively recognizing the protein, as well as a composition of one or more components, a solution, or an apparatus suitable for the analysis.

Further, the kit of the present invention may include a substrate, a suitable buffer solution, a coloring enzyme, or a secondary antibody labeled with a fluorescent substance, a coloring substrate, etc. for the immunological detection of antibody. As for the substrate, a nitrocellulose membrane, a 96-well plate made of polyvinyl resin, a 96-well plate made of polystyrene resin, a slide glass made of glass or the like may be used. As for the coloring enzyme, peroxidase, alkaline phosphatase or the like may be used. As for the fluorescent substance, FITC, RITC or the like may be used. As for the coloring substrate solution, ABTS (2,2'-azino-bis-(3-ethylbenzthiazoline-6-sulfonic acid)), OPD (o-phenylenediamine), or TMB (tetramethyl benzidine) may be used, but is not limited thereto. Moreover, for the analysis of protein levels, a method such as Western blotting, ELISA (Enzyme Linked Immunosorbent Assay), radioimmunoassay (RIA), radioimmunodiffusion, ouchterlony immunodiffusion, rocket immunoelectrophoresis, immunohistostaining, an immunoprecipitation assay, a complement fixation assay, FACS, a protein chip, etc. may be included, but is not limited thereto.

In still another aspect, the present invention provides a method of diagnosing a neurodegenerative disease selected from the group consisting of Parkinson's disease, dementia with Lewy bodies, and multiple system atrophy, including the step of measuring whether SHP-1/-2 or FcγRIIB is activated by using the diagnostic composition or kit.

Specifically, the method of diagnosing neurodegenerative diseases of the present invention may be performed by including the step of measuring whether SHP-1/-2 or FcγRIIB is activated in a biological sample separated from a subject suspected of having a neurodegenerative disease.

For a specific example, when the SHP-1/-2 or FcγRIIB is activated, it is determined that the subject has neurodegenerative diseases.

As used herein, the term "sample" is not particularly limited, as long as it shows a difference in SHP-1/-2 or FcγRIIB activation which is a diagnostic index of neurodegenerative diseases, and the sample may be one or more samples selected from the group consisting of nerve tissue-derived cells, whole blood, serum, blood, plasma, saliva, urine, sputum, lymphatic fluid, cerebrospinal fluid, and interstitial fluid, but is not limited thereto.

In the present invention, a method of measuring whether SHP-1/-2 or FcγRIIB is activated may include phagocytosis assay, Western blot, co-immunoprecipitation assay, ELISA (Enzyme Linked Immunosorbent Assay), real-time RT-PCR, electrophoresis, immunostaining, and FACS (fluorescence activated cell sorter), but is not limited thereto.

In still another aspect, the present invention provides a method of preventing or treating neurodegenerative disease by using the diagnostic composition or kit.

Specifically, the method of preventing or treating neurodegenerative disease provided in the present invention includes the steps of (a) diagnosing a neurodegenerative disease selected from the group consisting of Parkinson's disease, dementia with Lewy bodies and multiple system atrophy by measuring whether SHP-1/-2 or FcγRIIB is activated using the diagnostic composition or kit; and (b) administering with the pharmaceutical composition a subject who is diagnosed to have the neurodegenerative disease.

Hereinafter, the present invention will be described in more detail with reference to Examples. However, the following Examples are for illustrative purposes only, and the disclosure of the present invention is not intended to be limited by the following Examples.

Example 1. Aggregated α-Syn Inhibiting Microglial Phagocytosis in a Dose-Dependent Manner Example 1-1. Analysis of Effect of Aggregated α-Syn on Microglial Phagocytosis Recombinant α-synuclein (α-Syn) and aggregated α-syn were prepared. The recombinant α-Syn was overexpressed in *E. coli* strain BL21 (DE3), and the recombinant protein was purified by a known method (Lee, S. B., et al., 2009. Biochem Biophys Res Commun. 381, 39-43.). Purified α-syn protein was stored at −80° C. until use as monomeric α-syn. 2 mg/ml of monomeric α-syn was incubated at 37° C. with continuous agitation at 250 rpm for 2 weeks, and simply sonicated and stored at −80° C. until use as aggregated α-syn. The aggregated α-syn thus prepared was used in all Examples of the present invention.

Further, BV-2 cells, a murine microglial cell line, were grown in Dulbecco's modified Eagle's Medium (DMEM) supplemented with 5% fetal bovine serum (FBS) and maintained at 37° C. in a humidified atmosphere of 5% $CO_2$. Rat primary microglia from the cerebral cortices of 1-day-old Sprague-Dawley rats were cultured as described in the known literature (Kim, K. S., et al., 2012. J Biol Chem. 287, 24862-72.).

In order to explore the effect of aggregated α-syn on microglial phagocytosis, BV-2 cells, a murine microglial cell line, were treated with serial doses of aggregated α-syn and fluorescent microspheres for 12 hours, and phagocytic activity was analyzed by the following experiment (Park, J. Y., et al., 2008. Glia. 56, 1215-23.).

Briefly, BV-2 cells ($5 \times 10^4$ cells per well) were cultured in a 12 well plate overnight. The medium was then removed and replaced with fresh DMEM containing 5% FBS. 100 green fluorescent microspheres per cell and serial doses of aggregated α-syn were added to the cells and incubated for 2 hours or 12 hours. The cells were then washed three times with ice cold phosphate buffered saline (PBS) to remove residual cell surface-bound fluorescent microspheres, fixed with 4% paraformaldehyde. DNAs were stained by DAPI staining, and the stained DNAs are colored blue. The five random fields of cells (>100 cells) were counted under a confocal microscope (Zeiss, Germany). Percentage of phagocytic cells was analyzed by a known method (Park, J. Y., et al., 2008. Glia. 56, 1215-23.). For cell viability assay, BV-2 cells were treated with 1 µM of aggregated α-syn for 12 hours, and then LDH release was measured using an LDH-cytotoxicity assay kit (Biovision, CA) according to the manufacturer's instructions.

Figure 1C:
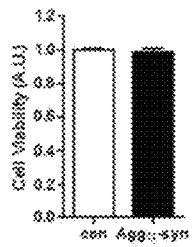
Figure 1D:
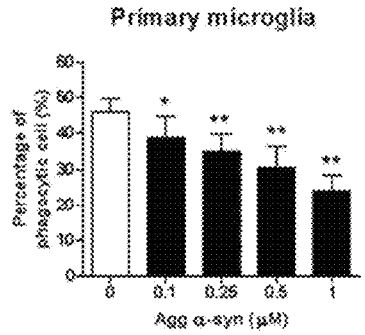

As shown in A and B of FIG. 1, the phagocytosis assay showed that aggregated α-syn inhibited phagocytosis of BV-2 cells in a dose-dependent manner, but this effect was not due to a decrease in cell viability (FIG. 1C). The same effect was also observed in rat primary microglia (FIG. 1D), which is in agreement with the finding in the previous study of the present inventors (Park, J. Y., et al., 2008. Glia. 56, 1215-23.).

Example 1-2. Analysis of α-Syn Form Inhibiting Phagocytic Function of Microglia

In order to explore which form of α-syn inhibits phagocytic activity of microglia, the present inventors collected α-syn at different time points of incubation. The aggregation status of α-syn was determined by a known Thioflavin T binding assay (Park, J. Y., et al., 2008. Glia. 56, 1215-23) and observed under electron microscopy.

Briefly, during incubation, small aliquots were taken and mixed with 20 µM of thioflavin T in 5× assay buffer (250 mM glycine (pH 8.5)) in a final volume of 200 µl, and the fluorescences were measured at 482 nm with an excitation at 446 nm (PerkinElmer Vitor3). In addition, 20 µl of aliquot of aggregated α-syn was adsorbed onto carbon-coated copper grid and air-dried for 20 minutes. After negative staining with 2% uranyl acetate for another 1 minute, aggregated α-syn was observed with an electron microscope (EM902A, Zeiss, Germany). Freshly prepared monomeric and aggregated α-syn have the same effect as monomeric and aggregated α-syn stored at −80° C.

Figure 1E:
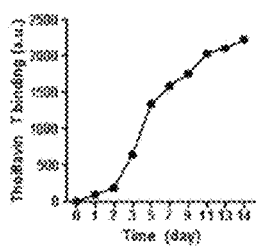
Figure 1F:
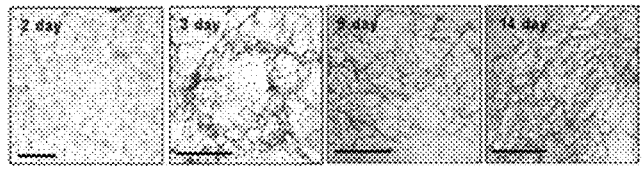

As shown in FIG. 1E, the results of the assay and microscopic analysis showed that thioflavin T binding to α-syn increased dramatically from 2 days of incubation and plateaued to some extent from 6 days (FIG. 1E). Electron microscopic analysis showed that the 2-day incubated α-syn was predominantly in the oligomeric form, the 3-day incubated α-syn was in the fibrillar form, although the oligomeric form of α-syn was still observed. The 14-day α-syn was only in the fibrillar form (FIG. 1F). These results indicate that under conditions of the present invention, aggregated α-syn is in the fibrillar form.

Next, a phagocytosis assay was performed using monomeric or aggregated forms of α-syn collected at different time points. In the previous study of the present inventors, the results of phagocytosis assay performed on 2-h incubated fluorescent microspheres showed a statistically significant activating effect of monomeric α-syn on microglial phagocytosis, but not the inhibitory effect of aggregated α-syn. In the present invention, however, phagocytosis assay performed on 12-h incubated fluorescent microspheres showed a statistically significant inhibitory effect of aggregated form of α-syn, which may be due to the sensitivity of phagocytosis assay. Therefore, the present inventors performed phagocytosis assay at 2 different time points.

Figure 1G:
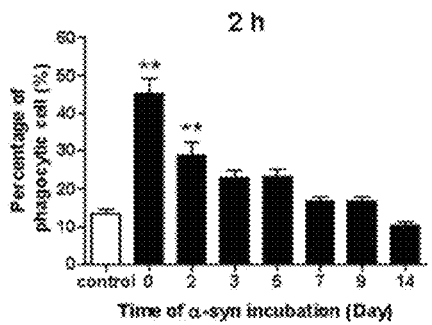
Figure 1H:
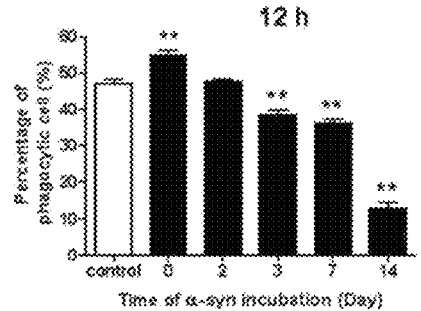

As shown in FIGS. 1G and H, monomeric α-syn increased microglial phagocytosis. However, α-syn inhibited microglial phagocytosis as the incubation time for preparing aggregated α-syn increased, suggesting that the inhibitory effect of aggregated α-syn on microglial phagocytosis is predominantly exerted by fibrillar α-syn.

Taken together, the results of Example 1 suggest that monomeric α-syn increases microglial phagocytosis, but aggregated α-syn in the fibrillar form inhibits microglial phagocytosis in a dose-dependent manner.

Example 2. Immune Complex (ICs)-Induced Phagocytosis Inhibited by Aggregated α-Syn Example 2-1. Analysis of Effect of Aggregated α-Syn on ICs-Induced Phagocytosis To explore the molecular mechanism by which aggregated α-syn inhibits microglial phagocytosis, the present inventors took advantage of ICs-induced phagocytosis whose signaling pathways have been relatively well studied.

To prepare ICs, the normal mouse IgG (Abcam, ab37355) and affinity-purified rat anti-mouse IgG Ab (Sigma, M8642) were incubated at a ratio of 1:100 for 30 minutes.

Thereafter, phagocytosis assay was performed in BV-2 cell and rat primary microglia in the same manner as in Example 1.

Figure 2A:
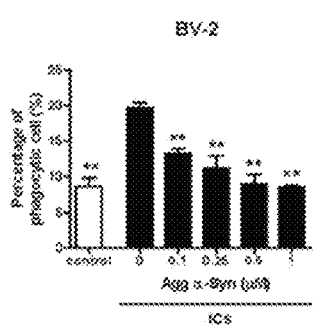
FIGS. 2A-2G show images and graphs showing that aggregated α-syn inhibits immune complex (ICs)-induced phagocytosis.
Figure 2B:
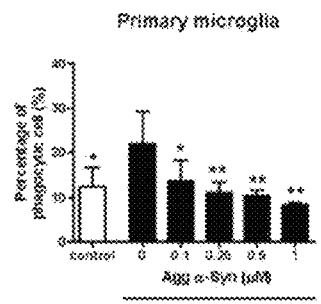

As shown in FIG. 2A, ICs induced phagocytosis in BV-2 cells and aggregated α-syn also inhibited ICs-induced phagocytosis in a dose-dependent manner. A similar effect was also observed in rat primary microglia (FIG. 2B).

Figure 2C:
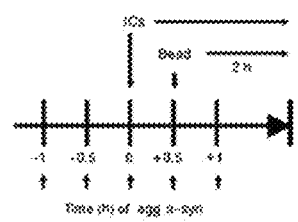

As shown in FIG. 2C, the present inventors performed a phagocytosis assay in the same manner as in Example 1, in order to investigate the effect of α-syn aggregated at different time points on microglial phagocytosis.

Figure 2D:
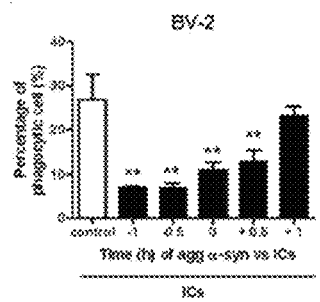
Figure 2E:
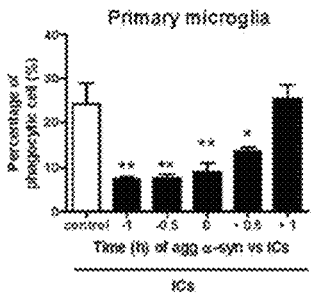

The results of assay showed that treatment with aggregated α-syn before ICs stimulation and 30 minutes after ICs stimulation inhibited ICs-induced phagocytosis in BV-2 cells; however, treatment with aggregated α-syn at 1 hour after ICs stimulation did not inhibit ICs-induced phagocytosis (FIG. 2D). A similar effect was also observed in primary microglia (FIG. 2E), suggesting that the inhibitory effect of aggregated α-syn on ICs-induced phagocytosis may occur at the early stage of ICs-induced signaling pathways.

Example 2-2. Analysis of Localization of ICs and α-Syn in Microglia

Next, in order to examine localization of aggregated α-syn and ICs in BV-2 cells, the present inventor performed immunostaining using anti-mouse IgG antibody (green)-conjugated Alexa 488 and anti-α-syn antibody (red)-conjugated Alexa 568, and analyzed using a confocal microscope.

For confocal microscopy, BV-2 cells cultured on coverslips were washed three times with PBS and fixed with 4% paraformaldehyde. The fixed cells were washed several times with PBS and incubated in the absence or presence of the permeabilization buffer (PBS containing 0.1% Triton X-100) for 1 minute at room temperature, and then incubated with mouse IgG antibody and α-syn antibody overnight at 4° C. Then, the prepared cells were stained with Alexa 488 or Alexa 594-conjugated secondary antibodies (Jackson Immunoresearch, West Grove, Pa.) for 2 hour, and then DNAs were stained blue by DAPI staining for 10 minutes. Then, the cells were mounted and observed under a confocal microscope.

Figure 2F:
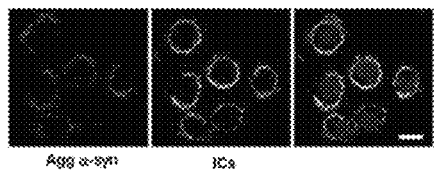

The results showed that aggregated α-syn bound to the plasma membrane in a clustered fashion was in agreement of the finding of the previous study of the present inventors, and the merged image showed that a small portion of aggregated α-syn was colocalized with ICs (FIG. 2F).

Example 2-3. Analysis of Correlation of Microglial Phagocytosis Receptor and α-Syn Phagocytosis is triggered by the interactions between ligands and specific receptors (the Fc receptors and the complement receptors which are expressed in phagocytes). In particular, phagocytosis induced by FcγRs is initiated by clustering of these receptors by IgG-opsonized immune complexes (ICs) and transducing the signals to enhance phagocytosis (Cox and Greenberg, 2001; Garcia-Garcia and Rosales, 2002). For this reason, to assess whether aggregated α-syn interferes with ICs binding to FcγRs on the plasma membrane, the present inventors stained ICs in the presence or absence of aggregated α-syn.

Figure 2G:
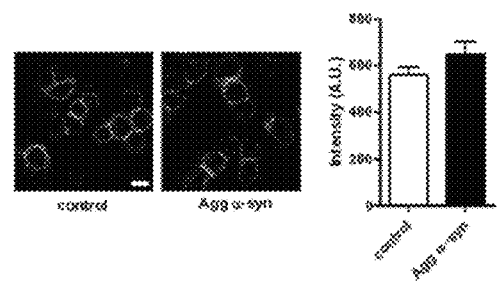

As shown in FIG. 2G, it was confirmed that aggregated α-syn did not interfere with ICs binding to the plasma membrane, suggesting that the inhibitory effect of aggregated α-syn on microglial phagocytosis is not due to the interference with ICs binding to FcγRs.

As shown in FIG. 2A, ICs induced phagocytosis in BV-2 cells, and aggregated α-syn inhibited ICs-induced phagocytosis in a dose-dependent manner. A similar effect was also observed in rat primary microglia (FIG. 2B).

Taken together, the results of Example 2 suggest that the inhibitory effect of aggregated α-syn on phagocytosis is determined at the early stage of ICs-induced signaling pathways, aggregated α-syn bound to the plasma membrane did not interfere with binding of ICs and FcγRs receptor, although colocalized with ICs, and therefore, inhibitory effect of aggregated α-syn on microglial phagocytosis is not due to the interference with ICs binding to FcγRs.

Example 3. Aggregated α-Syn Inhibiting ICs-Induced Signaling Pathway by SHP-1 Activation Example 3-1. Analysis of Effect of Aggregated α-Syn on Activity of Downstream Proteins of Phagocytosis Signaling Pathway ICs induce phagocytosis by cross-linking of FcγRs on the plasma membrane, which leads to the activation of Syk and further PLC-γ, triggering further downstream signaling events to induce phagocytosis (Nimmerjahn, F., Ravetch, J. V., 2008. Nat Rev Immunol. 8, 34-47.). To explore the level at which the ICs-FcγRs signaling pathway is inhibited by aggregated α-syn, the present inventors first performed Western blot to assess the activity of downstream proteins of the phagocytosis signaling pathway in BV-2 cell and rat primary microglia.

To performed Western blot, cells were lysed in ice-cold RIPA buffer (50 mM Tris-HCl, pH 7.4, 1% Nonidet P-40, 0.25% sodium deoxycholate, 150 mM NaCl) containing protease inhibitors (2 mM phenylmethylsulfonyl fluoride, 100 μg/ml leupeptin, 10 μg/ml pepstatin, 1 μg/ml aprotinin, and 2 mM EDTA) and phosphatase inhibitor cocktail (Gen-DEPOT, Baker, Tex.). The cells were lysed by sonication, and the lysates were centrifuged at 14,000 rpm for 30 min at 4° C. and the supernatant was collected. The protein concentrations were determined with a BCA protein assay kit. Proteins were resolved by SDS-PAGE, transferred to a nitrocellulose membrane, and immunoblotted with antibodies against pSyk, Syk pPLCγ, PLCγ, pSHP-1, SHP-1, pSHP-2, SHP-2, p-α-syn, α-syn and actin. They were then visualized using an enhanced chemiluminescence (ECL) system (Thermo, Waltham, Mass.).

Figure 3A:
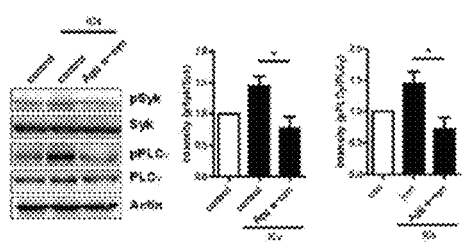
FIGS. 3A-3H are graphs and images showing that aggregated α-syn induces SHP-1 phosphorylation.
Figure 3B:
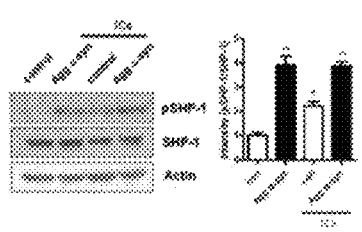
Figure 3C:
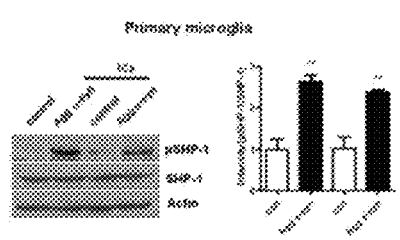
Figure 3D:
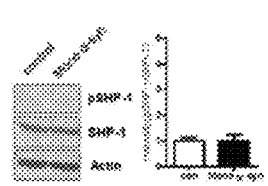
Figure 3E:
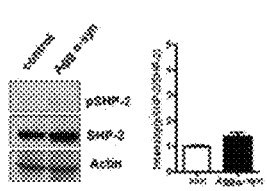

As shown in FIG. 3A, ICs induced the phosphorylation of Syk and PLCγ in BV-2 cells. However, aggregated α-syn inhibited ICs-induced phosphorylation of Syk and PLCγ, suggesting that aggregated α-syn inhibits ICs-induced signaling pathways upstream of Syk activation. Meanwhile, it was reported that ICs-FcγRs signaling pathways are inhibited by the recruitment of several phosphatases such as SHP-1 and SHP-2 (Scharenberg, A. M., Kinet, J. P., 1996. Cell. 87, 961-4.). Consistent with the results of the above study, aggregated α-syn of the present invention induced the phosphorylation of SHP-1 in both resting and ICs stimulation conditions (FIG. 3B). A similar effect was observed in rat primary microglia as in BV-2 cells (FIG. 3C). On the contrary, monomeric α-syn did not induce the phosphorylation of SHP-1 (FIG. 3D) and the phosphorylation of SHP-2 was also rarely induced by aggregated α-syn in BV-2 cells (FIG. 3E).

Example 3-2. Analysis of Localization of Downstream Proteins of Phagocytosis Signaling Pathway and Aggregated α-Syn in Microglia To investigate localization of the proteins related to phagocytosis signaling pathway in microglia, immunostaining was performed using green-colored anti-SHP-1 antibody and red-colored anti-α-syn antibody in the same manner as in Example 2, and observed by confocal microscopy.

Figure 3F:
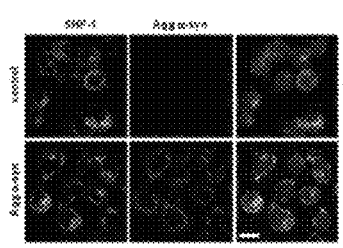
Figure 3G:
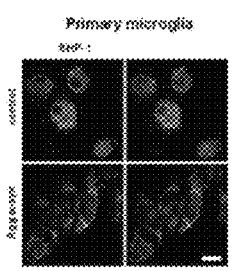

Confocal microscopic analysis indicated that in BV-2 cells, aggregated α-syn induced the translocation of SHP-1 to the plasma membrane, and SHP-1 translocated to the plasma membrane was colocalized with aggregated α-syn (FIG. 3F), which is also similar in primary microglia (FIG. 3G).

Example 3-3. Analysis of Effect of α-Syn on SHP-1 Phosphorylation at Whole Brain Level Furthermore, in the whole brain lysates of A53T heterozygous transgenic mice at the age of 9 months rather than at a cell level, the phosphorylation of SHP-1 was examined. The brain lysates were obtained by the following method.

Brains from C57BL6 A53T α-syn heterozygous transgenic mice and control C57BL6 mice at the age of 9 months were obtained as described in a known literature previously (Lee, H. J., et al., 2011. Exp Neurobiol. 20, 181-8.). Brain hemisphere was lysed by homogenizing in 600 μl ice-cold RIPA buffer containing protease inhibitor and phosphatase inhibitor cocktail. The lysates were incubated for 30 minutes at 4° C. Then, the lysates were centrifuged at 14,000 rpm for 30 minutes at 4° C. and the supernatant was collected for performing Western blot.

Figure 3H:
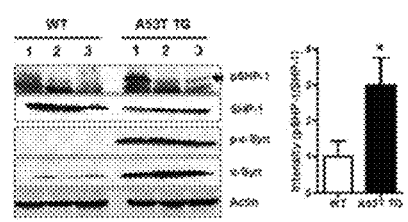

As a result, in the whole brain lysates of A53T heterozygous transgenic mice at the age of 9 months, the level of pSHP-1 which is phosphorylated SHP-1 was found to be increased, compared with that in the whole brain lysates of wild type (WT) mice (FIG. 3H). These results suggest that aggregated α-syn activates SHP-1, and thus may inhibit ICs-FcγRs signaling pathways through the recruitment of activated SHP-1 to the plasma membrane.

Taken together, the results of Example 3 suggest that aggregated α-syn inhibits ICs-induced signaling pathways upstream of Syk activation, and aggregated α-syn activates SHP-1, and the recruitment of activated SHP-1 to the plasma membrane inhibits ICs-FcγRs signaling pathways.

Example 4. SHP-1 Essential for the Inhibition of Microglial Phagocytosis by Aggregated α-Syn

Example 4-1. Analysis of Effect of Aggregated α-Syn on Phagocytosis of SHP-1 Knockdown (KD) Microglia To confirm the role of SHP-1 in the inhibition of microglial phagocytosis by aggregated α-syn, SHP-1 knockdown (KD) BV-2 cell line was prepared by the following method and used in the phagocytosis assay.

Transfection was performed using Lipofectamine 2000 (Invitrogen, Carlsbad, Calif.). SHP-1 knockdown BV-2 cells were prepared using lentiviral constructs expressing shRNA (Sigma, St. Louis, Mo.) by a known method. FcγRIIB knockdown (KD) BV-2 cell were also prepared using lentiviral constructs expressing shRNA (Yoon, S., et al., 2014. Cell Death Dis. 5, e1494.), and selected using puromycin.

Figure 4A:
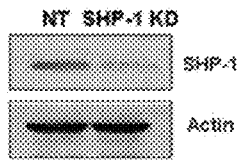
FIGS. 4A-4E show graphs and images showing that SHP-1 knockdown or NSC87877 treatment rescues the inhibitory effect of aggregated α-syn on microglial phagocytosis.
Figure 4B:
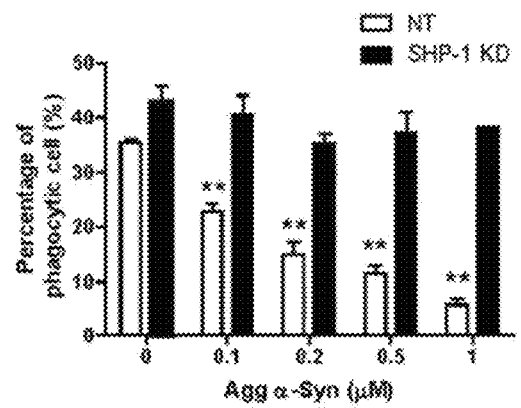
Figure 4C:
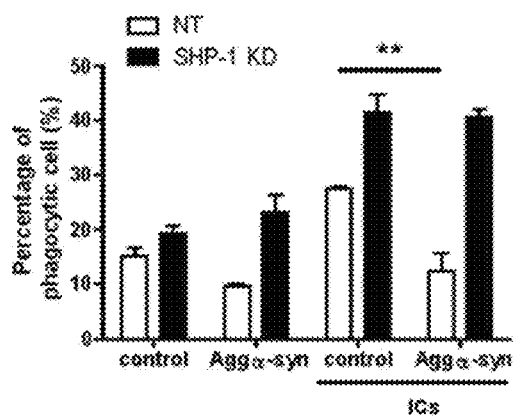

Further, SHP-1 expression levels in the prepared SHP-1 knockdown BV-2 cells were examined using SHP-antibody by Western blot in the same manner as in Example 3, and as a result, SHP-1 expression was efficiently reduced in the prepared SHP-1 knockdown BV-2 cells (FIG. 4A). As shown in FIG. 4B, aggregated α-syn inhibited phagocytosis efficiently in the BV-2 cell line, which was created by non-targeting (NT) shRNA as a normal comparison group; however, it did not inhibit phagocytosis in SHP-1 KD BV-2 cells. Also, ICs-induced phagocytosis which was inhibited by aggregated α-syn was also rescued in SHP-1 KD BV-2 cells (FIG. 4C).

Example 4-2. Analysis of Effect of SHP-1 Inhibitor on Microglial Phagocytosis Inhibited by Aggregated α-Syn Furthermore, the present inventors treated BV-2 cell and primary microglia with NSC87877 which is an SHP-1 expression inhibitor, and performed phagocytosis assay in the same manner as in Example 1.

Figure 4D:
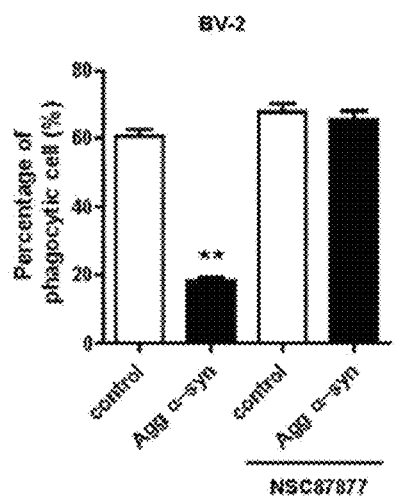
Figure 4E:
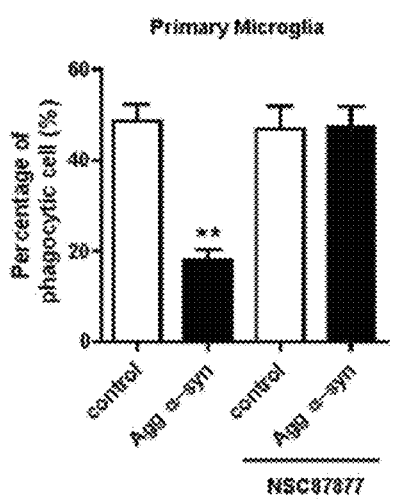

As shown in FIGS. 4D and 4E, the inhibition of SHP-1 by NSC87877 efficiently rescued the inhibitory effect of aggregated α-syn on microglial phagocytosis, suggesting that SHP-1 activation by aggregated α-syn is essential for the inhibition of microglial phagocytosis by aggregated α-syn.

Taken together, the results of Example 4 showed that treatment of SHP-1 knockdown microglia with aggregated α-syn did not inhibited phagocytosis of the cells, and the SHP-1 inhibitor NSC87877 efficiently rescued microglial phagocytosis inhibited by aggregated α-syn, suggesting that SHP-1 activation by aggregated α-syn is essential for the inhibitory effect of aggregated α-syn on microglial phagocytosis.

Example 5. Aggregated α-Syn Interacting with FcγRIIB

Example 5-1. Analysis of Correlation Between FcγRIIB and Aggregated α-Syn in Fibroblast Cell Line COS-7

Next, the present inventors focused on FcγRIIB, because it is known that FcγRIIB is an inhibitory receptor causing the inhibition of ICs-FcγRs signaling pathways (Nimmerjahn, F., Ravetch, J. V., 2006. Immunity. 24, 19-28.). Vectors of pCDNA3.1(−) myc.His murine FcγRIIB, FcγRI, and SIRPα were constructed by PCR using cDNA obtained from BV-2 cells, and transfected to COS-7 cells. As confirmed in the above Examples, exogenously added aggregated α-syn was mostly localized to the plasma membrane of microglia (FIG. 2G). Accordingly, intracellular SHP-1 activation by aggregated α-syn may be mediated by a certain component of the plasma membrane. To identify the mediator on the plasma membrane of microglia, the present inventors first treated COS-7 cell which is a monkey kidney-derived fibroblast cell line, namely, other than microglia, with aggregated α-syn, and examined whether it binds to the plasma membrane. Furthermore, to examine whether aggregated α-syn binds to the plasma membrane when FcγRIIB, FcγRI, and SIRPα are expressed in cells, immunostaining was performed in the same manner as in Example 3. COS-7 cells were transfected with myc-tagged FcγRIIB, FcγRI and SIRPα. After incubation for 1 day, the cells were incubated with 1 μM of aggregated α-syn for 30 minutes, and then fixed and immunostained with anti-myc (green) and anti-α-syn (red) antibodies. The cells were observed under confocal microscopy.

Figure 5A:
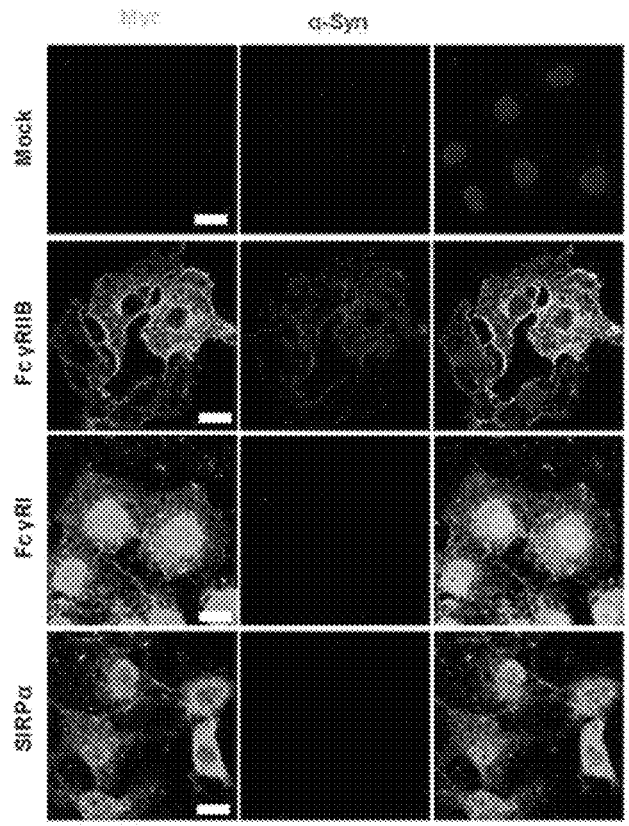
FIGS. 5A-5B show images of FcγRIIB which is specifically interacted with aggregated α-syn.

Aggregated α-syn did not bind to the plasma membrane of COS-7 cells, and aggregated α-syn bound to the plasma membrane of only COS-7 cells where FcγRIIB was expressed, and did not bind to the plasma membrane of COS-7 cells where FcγRI and SIRPα were expressed (FIG. 5A). These results suggest that aggregated α-syn may bind to a specific component of the plasma membrane of microglia but not to that of COS-7 cells.

As a result, aggregated α-syn bound to the plasma membrane of COS-7 cells. However, when FcγRI, a high-affinity activating FcγR, was transfected into COS-7 cells, aggregated α-syn did not bind on the plasma membrane of COS-7 cells (FIG. 5A).

These results suggest that aggregated α-syn may bind to a specific component of the plasma membrane of microglia but not to that of COS-7 cells.

To examine which protein interacts with aggregated α-syn, co-immunoprecipitation assay was performed. COS-7 cells were transfected with myc-tagged FcγRIIB and FcγRI, followed by incubation for one day. The cells were incubated with 1 μM of aggregated α-syn or monomeric α-syn for 30 minutes. 500 μg of each supernatant was incubated with 1 μg of myc antibody and α-syn antibody overnight at 4° C., and then adsorbed to protein G-Agarose (Millipore, Temecula, Calif.). After extensive washing with ice cold RIPA buffer, the samples were heated in 2×SDS-PAGE sample buffer for 5 min and subjected to gel electrophoresis on SDS-PAGE gels, followed by Western blot.

Figure 5B:
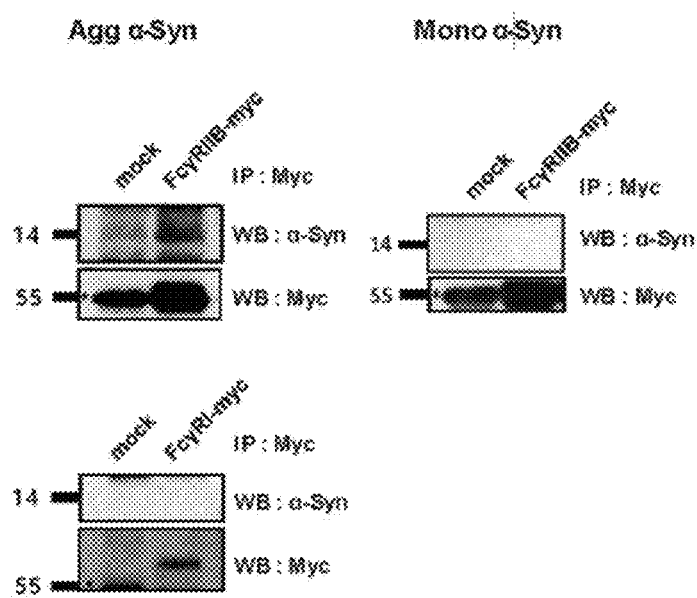

The results of the assay showed that aggregated α-syn interacted with FcγRIIB, but not FcγRI, and monomeric α-syn did not interact with FcγRIIB (FIG. 5B), suggesting that FcγRIIB is a specific receptor for aggregated α-syn, which causes inhibition of microglial phagocytosis.

Example 5-2. Analysis of Correlation Between FcγRIIB and Aggregated α-Syn in Microglia To confirm the involvement of FcγRIIB in the regulation of microglial phagocytosis by aggregated α-syn, the present inventors examined FcγRIIB expression levels using 2 different FcγRIIB knockdown BV-2 cell lines.

Western blot was performed in the same manner as in Example 3, and as a result, it was confirmed that FcγRIIB expression was efficiently suppressed in two different FcγRIIB KD BV-2 cell lines (FIG. 6A).

Further, phagocytosis assay was performed in the same manner as in Example 1, and as a result, as shown in FIG. 6B, aggregated α-syn inhibited microglial phagocytosis efficiently in the control group (con) and the normal comparison group (Non-targeting; NT) BV-2 cell. However, it rarely inhibited phagocytosis in both different FcγRIIB KD BV-2 cell lines.

In addition, immunostaining was performed in the same manner as in Example 2, and as a result, it was confirmed that aggregated α-syn bound less efficiently to the plasma membrane of FcγRIIB KD BV-2 cell lines than to the plasma membrane of the control group (con) and the normal comparison group (NT) BV-2 cell (FIG. 6C). Aggregated α-syn-induced phosphorylation of SHP-1 was also suppressed in FcγRIIB KD BV-2 cell lines (FIG. 6D). These results suggest that aggregated α-syn inhibits microglial phagocytosis by SHP-1 activation via FcγRIIB.

The present inventors examined FcγRIIB expression levels in BV-2 cells which were incubated with 1 μM of aggregated α-syn and 1 μM of monomeric α-syn for 6 hours by quantitative real-time RT-PCR.

BV-2 cells (2 to 3×10$^5$ cells per well) were plated in 6-well plates and treated with 1 μM of α-syn. Total RNA was extracted from cells using Trizol reagent (Invitrogen, Carlsbad, Calif.), and cDNA was prepared using avian myeloblastosis virus reverse transcriptase (Promega, Madison, Wis.) according to the manufacturer's instructions. cDNA samples were analyzed using a Rotor-Gene SYBR Green PCR Master mix kit on Rotor-Gene cyclers (Qiagen, Valencia, Calif.) with specific primers: forward: 5'-CATGTTT-GAGACCTTCAACA-3' (SEQ ID NO: 1) and reverse: 5'-GCCATCTCCTGCTCGAAGTC-3' (SEQ ID NO: 2) for murine FcγRIIB, and forward: 5'-GGTTCCAGCTCTC-CCAGG-3' (SEQ ID NO: 3) and reverse: 5'-TTCATCCA-GGGCTTCGGG-3' (SEQ ID NO: 4) for murine Actin. All values were calculated using the delta Ct method and expressed as a change relative to expression of Actin mRNA.

It was confirmed that aggregated α-syn induced FcγRIIB expression (FIG. 6E), but monomeric α-syn did not (FIG. 6F). Furthermore, Western blot was performed to confirm that aggregated α-syn induced FcγRIIB expression (FIG. 6G).

Further, FcγRIIB expression in the whole brain rather than in cells was examined by Western blot. As a result, in the whole brain lysate of A53T TG mice, FcγRIIB expression was increased, compared with that in the brain lysates of WT mice (FIG. 6H).

Example 5-3. Aggregated α-Syn Binding to Plasma Membrane of HEK293 Kidney Cell Line and SHSY5Y Cell Line In order to investigate the mechanism of action of aggregated α-syn on nerve cells, a human dopaminergic neuroblastoma cell line SH-SY5Y and a human kidney cell line HEK293 were treated with aggregated α-syn.

As a result, it was confirmed that α-syn bound to the plasma membrane of human dopaminergic neuroblastoma cell line SH-SY5Y cell (FIG. 7A), which was different from the phenomenon in human kidney cell line, COS-7 or HEK293. These results suggest that receptors capable of binding with aggregated α-syn exist on microglia or nerve cells, unlike COS-7 cells or HEK293 cells, and signals are transduced via these receptors (FIG. 7). As confirmed in the above result that aggregated α-syn bound less efficiently to the plasma membrane of FcγRIIB KD BV-2 cell lines than to the plasma membrane of the normal comparison group (NT) BV-2 cell (FIG. 6C), binding of aggregated α-syn to the plasma membrane was reduced in FcγRIIB KD SHSY5Y (FIG. 7B).

Taken together, the results of Example 5 suggest that FcγRIIB is an aggregated α-syn-specific receptor, and binding of aggregated α-syn to FcγRIIB activates SHP-1 to inhibit microglial phagocytosis.

Example 6. Effect of FcγRIIB on Neurotoxicity of Aggregated α-Syn

To investigate neurotoxicity by aggregated α-syn, SH-SY5Y cells differentiated to dopaminergic neurons with retinoic acid were treated with aggregated α-syn, and then cytotoxicity was assessed.

To differentiate SH-SY5Y cells to dopaminergic neurons, SH-SY5Y cells seeded in a culture plate were cultured in a medium containing 50 μM of retinoic acid for 5 days. In this regard, the medium was replaced by a fresh medium containing 50 μM of retinoic acid at 3 days, 4 days, and 5 days after initiation of the culture. Further, in order to assess cytotoxicity, the differentiated SH-SY5Y dopaminergic neurons and undifferentiated SH-SY5Y dopaminergic neurons were seeded in 12 wells, respectively, followed by incubation for one day.

Figure 8A:
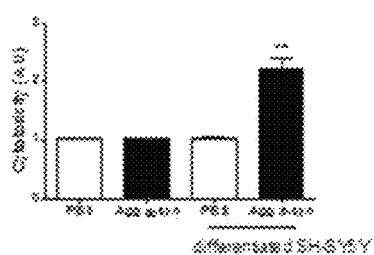
FIGS. 8A-8C show images and graphs showing the effect of FcγRIIb on neurotoxicity of α-syn.

As a result, it was confirmed that aggregated α-syn exhibited cytotoxicity only under differentiation conditions of dopaminergic neurons. Death of dopaminergic neurons is one of the features of Parkinson's disease, and the above results suggest that aggregated α-syn may be a cause of Parkinson's disease (FIG. 8A).

Figure 8B:
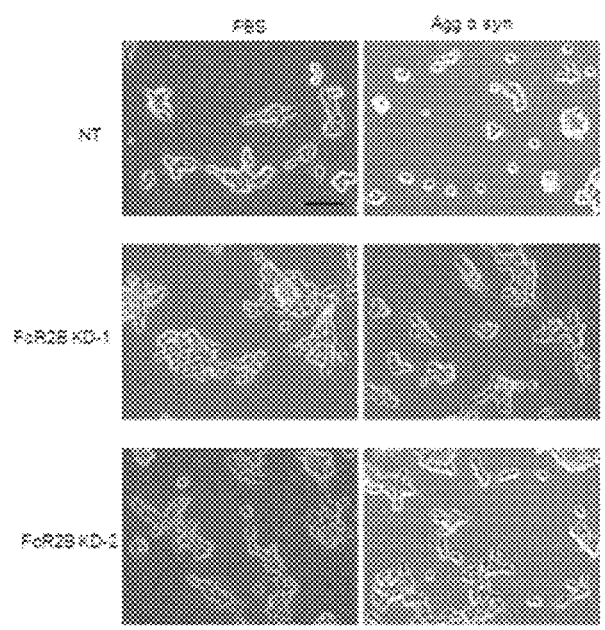
Figure 8C:
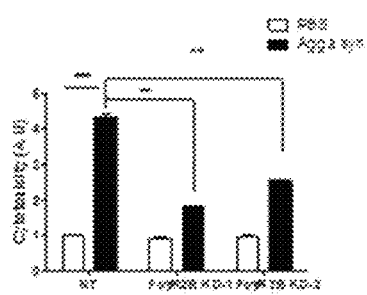

Furthermore, to investigate whether cytotoxicity of aggregated α-syn is mediated by FcγRIIB, two FcγRIIB knockdown SHSY5Y cell lines were prepared. FcγRIIB knockdown SHSY5Y cells differentiated to dopaminergic neurons with retinoic acid were treated with aggregated α-syn, and then cytotoxicity was assessed. As a result, cytotoxicity by α-syn was observed in normal comparison (NT) cell line, whereas cytotoxicity was reduced in FcγRIIB KD1 and FcγRIIB KD2 cell lines (FIGS. 8B and 8C).

Taken together, the results of Example 6 suggest that aggregated α-syn binds to FcγRIIB on differentiated SHSY5Y to show cytotoxicity.

Example 7. Effect of FcγRIIb on Translocation of α-Syn into Cells

In order to investigate whether FcγRIIB is involved in translocation of α-syn into cells, α-syn-overexpressed SH-SY5Y dopaminergic neuron and FcγRIIB knockdown SH-SY5Y cells were co-cultured in the same manner as in Example 6-1, and examined by immunostaining.

Figure 9A:
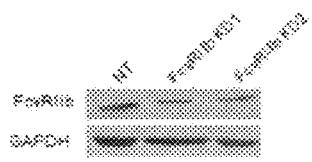
FIGS. 9A-9G are immunostaining images showing the effect of FcγRIIb on intracellular translocation of α-syn.
Figure 9B:
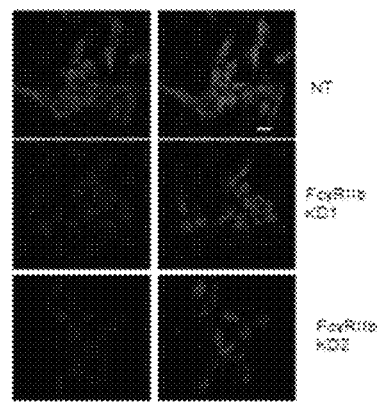
Figure 9C:
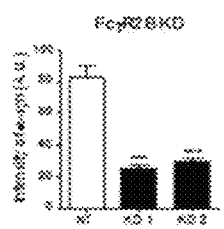

As a result, it was confirmed that translocation of α-syn released from α-syn-overexpressed SH-SY5Y cells was reduced in FcγRIIB knockdown SH-SY5Y cells (FIG. 9B). These results suggest that FcγRIIB is involved in the translocation of α-syn released from different cells into neighboring cells.

Figure 9D:
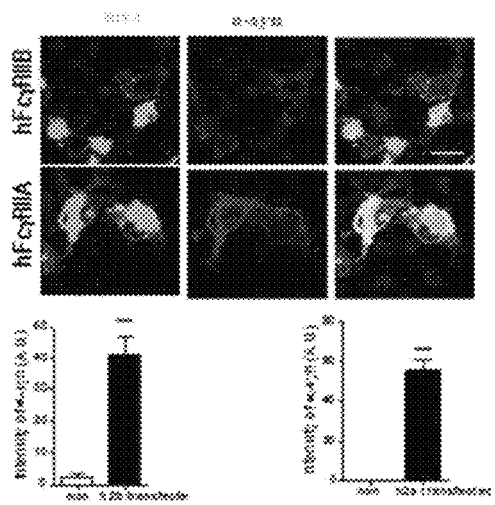
Figure 9E:
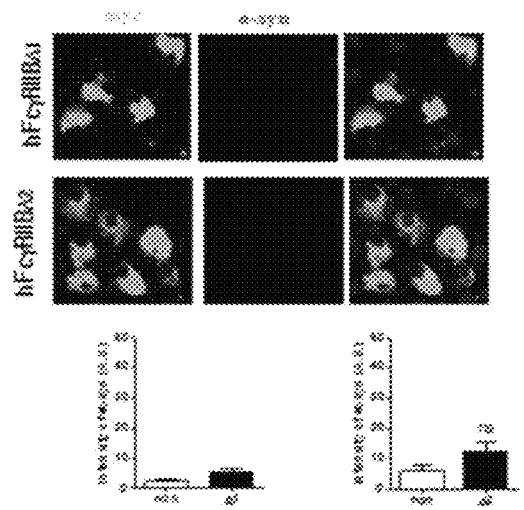

In order to further investigate the above results, Cos7 cells were transfected with myc-tagged hFcγRIIB, followed by incubation for one day. Thereafter, co-culture was performed in the same manner as in Example 6-1, followed by immunostaining. As a result, it was confirmed that α-syn propagation between hFcγRIIB-transfected cells and non-transfected cells was increased (FIGS. 9D and 9E).

Figure 9F:
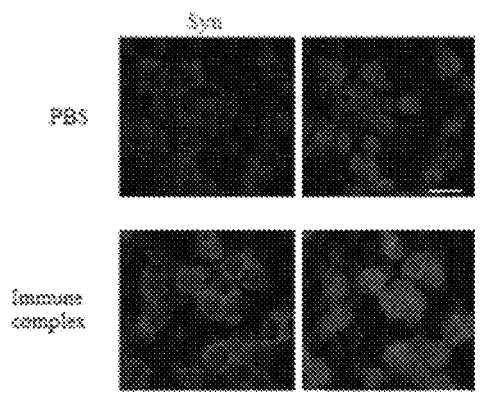
Figure 9G:
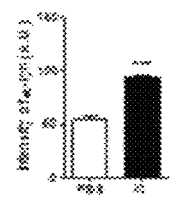

Lastly, in order to investigate whether α-syn translocation is mediated by FcγRIIB, FcγRIIB on SHSY5Y cells was activated by ICs. As a result, it was confirmed that α-syn propagation was increased by FcγRIIB activated by ICs (FIGS. 9F and 9G).

Taken together, the results of Example 7 suggest that translocation of α-syn into cells is mediated by FcγRIIB.

Example 8. Effect of SHP-1 on α-Syn Propagation

Example 8-1. Effect of SHP-1 on α-Syn Propagation, Confirmed in SHP-1 Knockdown Cell Line In order to investigate how SHP-1 activation by aggregated α-syn affects α-syn propagation, the present inventors prepared two SHP-1 knockdown SH-SY5Y cell lines (SHP-1 KD1 and SHP-1 KD2), and two BV2 cell lines and one OLN 93 cell line were prepared, and used in the analysis of α-syn propagation.

The prepared SHP-1 knockdown SH-SY5Y dopaminergic neuronal cell lines (SHP-1 KD1 and SHP-1 KD2) were co-cultured with α-syn-overexpressed SH-SY5Y dopaminergic neuronal cell line using the two-chamber system for 12 hours. The co-culture is briefly summarized as follows. SH-SY5Y or BV2 or OLN93 cell was seeded at a density of $4 \times 10^4$ cell per well on a 12-well cover glass, and α-syn-overexpressed SH-SY5Y cell was seeded at a density of $4 \times 10^4$ cell per well on a 12-well transwell. Each of the cells was incubated for one day, and then the transwell (α-syn-overexpressed SH-SY5Y cell) was transferred to the 12-well cover glass (SH-SY5Y cell), followed by co-culture for 12 hours, and then immunostaining.

Figure 10A:
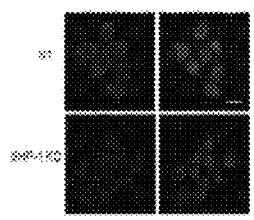
FIGS. 10A-10P are images showing that SHP-1 activated by phosphorylation is involved in propagation of aggregated α-syn to neighboring cells. Scale bar indicates 20 μm. The red color indicates propagated α-syn, and the blue color indicates DNA in cells.
Figure 10B:
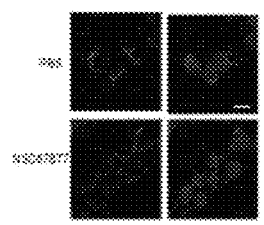
FIGS. 10B and 10E are images and graphs showing that α-syn propagation was reduced by treatment of SHP-1/2 inhibitor, NSC87877. *** P<0.001 represents a comparison with the PBS-treated group.
Figure 10C:
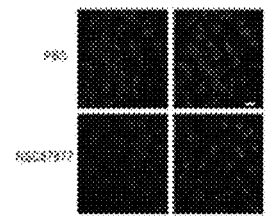
FIGS. 10C and 10F are images and graphs showing that α-syn propagation was reduced in rat microglia by treatment of the SHP-1/2 inhibitor, NSC87877. Scale bar indicates 20 μm, and *** P<0.001 represents a comparison with the PBS-treated group.
Figure 10D:
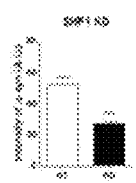
Figure 10E:
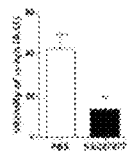
Figure 10F:
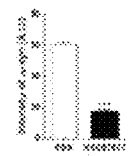
Figure 10G:
FIG. 10G is an image showing the results of Western blot for SHP-1 by aggregated α-syn in a dopaminergic neuronal cell line, SH-SY5Y.
Figure 10H:
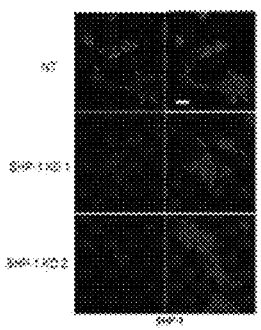
FIGS. 10H and 10J are images and graphs showing that propagation of aggregated α-syn is reduced in SHP-1 KD1 and SHP-1 KD2 cell lines when two SHP-1 knockdown SH-SY5Y cell lines (SHP-1 KD1, SHP-1 KD2) were co-cultured with α-syn-overexpressed SH-SY5Y dopaminergic neuronal cell line. *** P<0.001 represents a comparison with the control group.
Figure 10I:
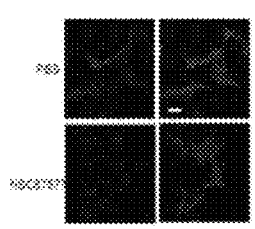
FIGS. 10I and 10K are images and graphs showing that propagation of aggregated α-syn is reduced in SH-SY5Y cell line treated with the SHP-1,2 inhibitor NSC87877, similar to the SHP-1 knockdown cells. *** P<0.001 represents a comparison with the PBS-treated group.
Figure 10J:
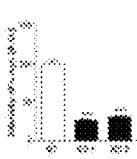
Figure 10K:
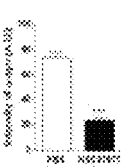
Figure 10L:
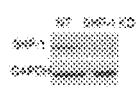
FIG. 10L is an image showing the result of Western blot of SHP-1 in an SHP-1 knockdown OLN 93 cell line.
Figure 10M:
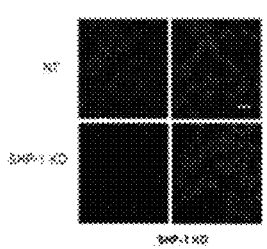
FIGS. 10M and 10O are images and graphs showing that propagation of α-syn is reduced in the SHP-1 knockdown OLN 93 cell line. Scale bar indicates 20 μm, and *** P<0.001 represents a comparison with the control group.
Figure 10N:
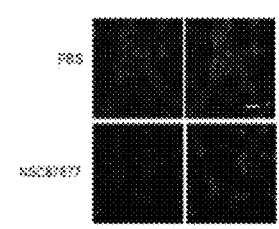
Figure 10O:
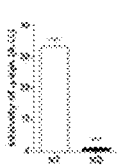
Figure 10P:
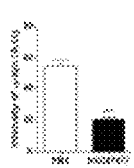

As a result, it was confirmed that α-syn propagation was observed in the normal comparison cell line (NT), whereas α-syn propagation was reduced in SHP-1 KD1 and SHP-1 KD2 cell lines (FIGS. 10A, 10H and 10M). In order to further investigate the result, the SHP-1,2 inhibitor NSC87877 was treated. As a result, α-syn propagation was also reduced, which is similar to the results in SHP-1 knockdown BV-2, SHSY5Y and OLN93 cells (FIGS. 10B, 10I and 10N). Further, when primary microglia was treated with the SHP-1,2 inhibitor NSC87877, reduced α-syn propagation was observed (FIG. 10C)

Example 8-2. SHP-1 Activation by Aggregated α-Syn, Confirmed in Nerve Cells

In order to investigate the mechanism of action of aggregated α-syn on nerve cells, a human dopaminergic neuroblastoma cell line SH-SY5Y and a human kidney cell line HEK293 were treated with aggregated α-syn.

Figure 11A:
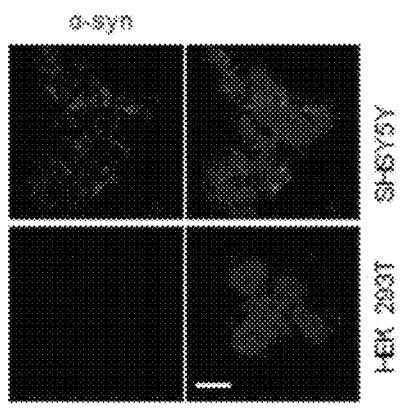
FIGS. 11A-11F are images showing that receptors capable of binding with aggregated α-syn exist on the plasma membrane of nerve cells, and signals are transduced via the receptors.
Figure 11B:
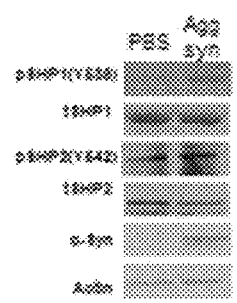
Figure 11C:
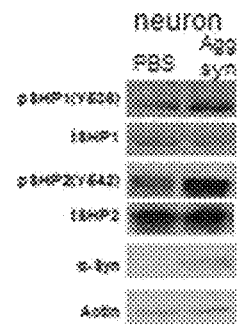
Figure 11D:
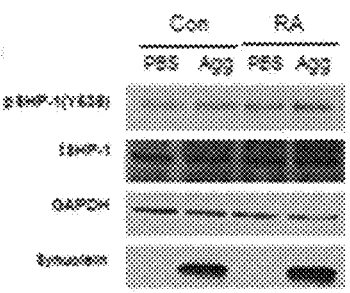
Figure 11E:
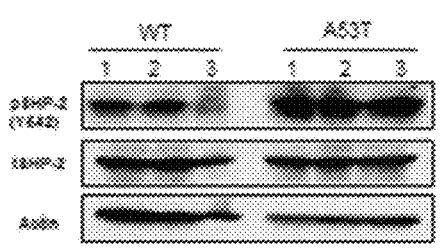
Figure 11F:
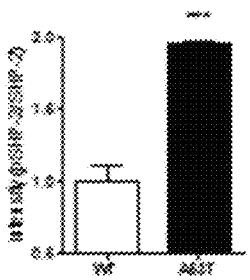

As a result, it was confirmed that α-syn bound to the plasma membrane of human dopaminergic neuroblastoma cell line SH-SY5Y cell (FIG. 11A), and SHP-1 phosphorylation was also increased (FIG. 11B), which was different from the phenomenon in human kidney cell line, COS-7 or HEK293. These results suggest that receptors capable of binding with aggregated α-syn exist on microglia or nerve cells, unlike COS-7 cells or HEK293 cells, and signals are transduced via these receptors (FIG. 11). Further, SHP-1 phosphorylation increased by aggregated α-syn was also observed in neurons (FIG. 11C), and SHP-1 phosphorylation was increased in differentiated SHSY5Y, compared to undifferentiated SHSY5Y (FIG. 11D), and SHP-1 phosphorylation was further increased by aggregated α-syn in differentiated SHSY5Y, compared to undifferentiated SHSY5Y (FIG. 11D). Further, phosphorylation of SHP-2 having homology to SHP-1 was also increased by aggregated α-syn in SHSY5Y (FIG. 11B), primary neuron (FIG. 11C) and A53T Transgenic mice (FIGS. 11E and 11F). As previously confirmed, SHP-1 activation was increased by aggregated α-syn, but SHP-2 activation was not in rat microglia and BV2. However, in SHSY5Y and nerve cells and in A53T brain lysates, both SHP-1 activation and SHP-2 activation were increased, indicating that there is a difference in the effects of aggregated α-syn between microglia and nerve cells.

Taken together, the results of Example 8 suggest that SHP-1 activation by phosphorylation occurs by aggregated α-syn in microglia, and SHP-1 activation by phosphorylation and SHP-2 activation by phosphorylation occur also in nerve cells.

Example 9. Effect of SHP-1 on Neurotoxicity of α-Syn

To investigate neurotoxicity by aggregated α-syn, SH-SY5Y cells differentiated to dopaminergic neurons with retinoic acid were treated with aggregated α-syn, and then cytotoxicity was assessed.

To differentiate SH-SY5Y cells to dopaminergic neurons, SH-SY5Y cells seeded in a culture plate were cultured in a medium containing 50 μM of retinoic acid for 5 days. In this regard, the medium was replaced by a fresh medium containing 50 μM of retinoic acid at 3 days, 4 days, and 5 days after initiation of the culture. Further, in order to assess cytotoxicity, the differentiated SH-SY5Y dopaminergic neurons and undifferentiated SH-SY5Y dopaminergic neurons were seeded in 12-well, respectively, followed by incubation for one day. Thereafter, they were cultured in a medium containing 1 μM of aggregated α-syn and 50 μM of the SHP-1/-2 inhibitor NSC87877 for 2 days, and LDH (lactate dehydrogenase) release assay was performed according to the manufacturer's instructions.

Figure 12A:
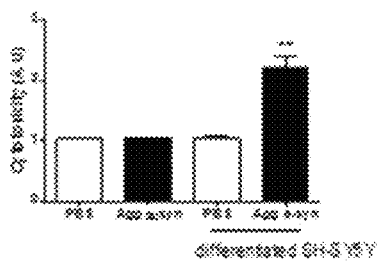
FIGS. 12A-12F show images and graphs showing the effects of SHP-1 on neurotoxicity by α-syn.

As a result, it was confirmed that aggregated α-syn exhibited cytotoxicity only under differentiation conditions of dopaminergic neurons (FIG. 12A). Death of dopaminergic neurons is one of the features of Parkinson's disease, and the above results suggest that aggregated α-syn may be a cause of Parkinson's disease.

Figure 12B:
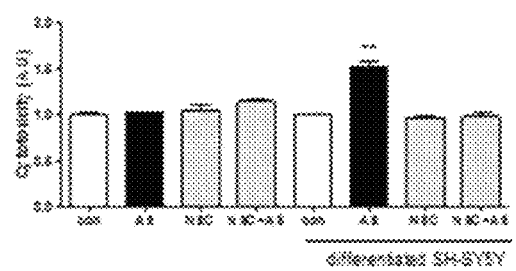
Figure 12C:
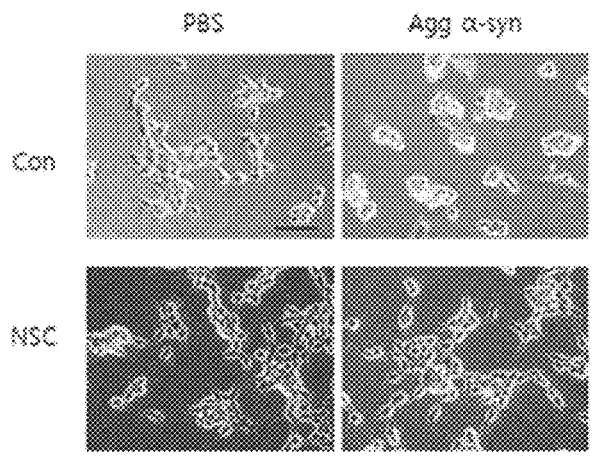
Figure 12D:
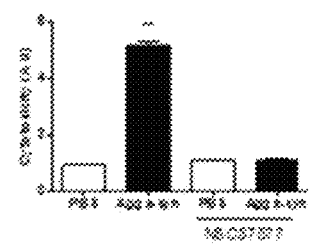
Figure 12E:
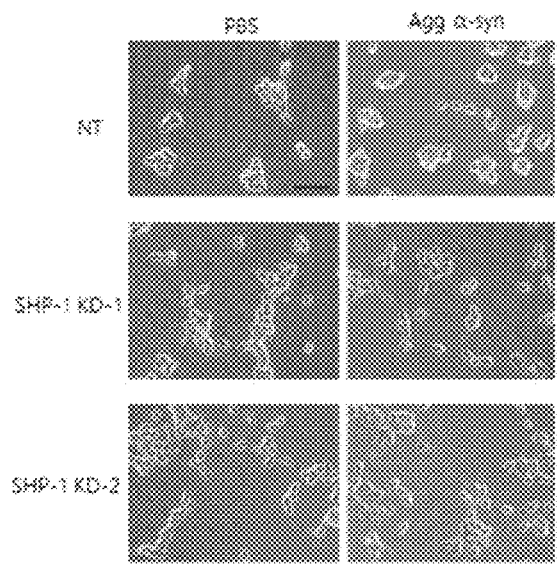
Figure 12F:
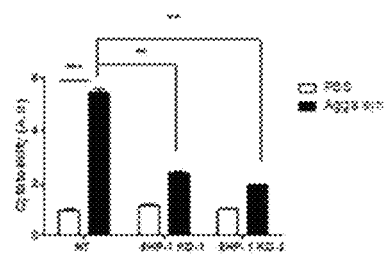

Furthermore, to investigate whether SHP-1 activation is involved in neurotoxicity by aggregated α-syn in differentiated nerve cells, the SHP-1/2 inhibitor NSC87877 was treated at the same time. As a result, it was confirmed that neurotoxicity by aggregated α-syn was reduced, suggesting that SHP-1 activation may be involved in neurotoxicity by aggregated α-syn (FIG. 12B). Further, to investigate whether neurotoxicity by aggregated α-syn is attributed to SHP-1, two SHP-1 knockdown SHSY5Y cell lines were prepared. SHP-1 knockdown SH-SY5Y cells differentiated to dopaminergic neurons with retinoic acid were treated with aggregated α-syn, and then cytotoxicity was assessed. As a result, cytotoxicity by α-syn was observed in the normal comparison cell (NT) whereas cytotoxicity was reduced in SHP-1 KD1 and SHP-1 KD2 cell lines (FIGS. 12C and 12D).

Taken together, the results of Example 9 suggest that differentiated SHSY5Y cells died by aggregated α-syn, which did not occur in undifferentiated SHSY5Y. Consequently, it can be seen that SHP-1 is involved in cytotoxicity of aggregated α-syn.

Example 10. Effects of SHP-1 and SHP-2 on Translocation of α-Syn into Cells

In order to investigate whether SHP-1 activation affects α-syn propagation, eGPF-tagged SHP-1 WT, eGPF-tagged SHP-1 active mutant form (SHP-1ΔN) and eGPF-tagged SHP-1 inactive mutant form (SHP-1C453S) were prepared, respectively, and then introduced into SHSY5Y cells. Thereafter, α-syn-overexpressed SH-SY5Y cells and SHP-1 WT, SHP-1 active (SHP-1ΔN) or inactive (SHP-1C453S) mutant form-transfected SH-SY5Y cells were incubated in a two-chamber system for 12 hours.

Figure 13A:
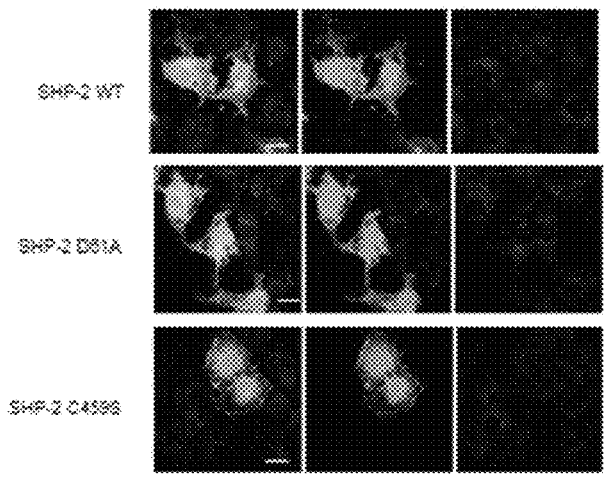
FIGS. 13A-13D show images and graphs showing whether SHP-1 activation affects propagation of α-syn. α-syn-overexpressed SH-SY5Y cells and eGFP-tagged SHP-1 and SHP-2 mutant form-expressed SH-SY5Y cells or cos7 cells were cultured using the two-chamber system for 12 hours. Thereafter, to investigate translocation of α-syn released from SH-SY5Y into the eGFP-tagged SHP-1 and SHP-2 mutant form-overexpressed cells, alpha-synuclein antibody was used to perform immunostaining. The red color indicates propagated α-syn, the blue color indicates DNA, and the green color indicates overexpression of SHP-1/2 mutant forms. Con indicates the control SH-SY5Y cell where the SHP-1/2 mutant forms were not overexpressed. Scale bar indicates 20 μm.
Figure 13B:
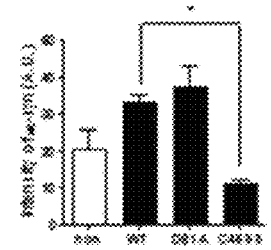
Figure 13C:
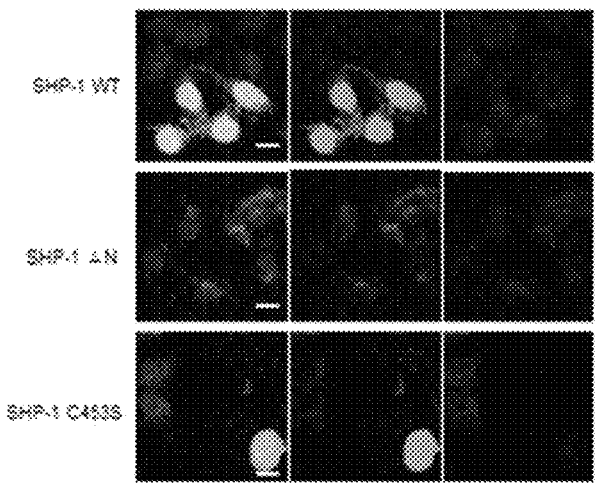
Figure 13D:
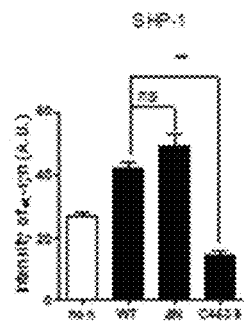

As a result, α-syn propagation was increased in the cells transfected with the SHP-1 active mutant form (SHP-1ΔN), whereas α-syn propagation was decreased in the cells transfected with the SHP-1 inactive mutant form (SHP-1 C453S) (FIGS. 13C and 13D).

In order to investigate whether SHP-2 activation affects α-syn propagation, eGPF-tagged SHP-2 WT, eGPF-tagged SHP-2 active mutant form (SHP-2 D61A) and eGPF-tagged SHP-2 inactive mutant form (SHP-2 C459S) were prepared, respectively, and then introduced into Cos7 cells. Thereafter, α-syn-overexpressed SH-SY5Y cells and SHP-2 active or inactive mutant form-transfected Cos7 cells were incubated in a two-chamber system for 12 hours.

As a result, α-syn propagation was increased in the cells transfected with the SHP-2 active mutant form (SHP-2 D61A), whereas α-syn propagation was decreased in the cells transfected with the SHP-1 inactive mutant form (SHP-1 C453S) (FIGS. 13A and 13B). In this regard, in order to investigate α-syn translocated into SH-SY5Y cells or cos7 cells, alpha-synuclein antibody was used to perform immunostaining. The red color indicates propagated α-syn, the green color indicates eGFP, and the blue color indicates DNA.

Taken together, the results of Example 10 suggest that α-syn propagation occurs by active SHP-1 or SHP-2, and α-syn propagation does not occur when SHP-1 or SHP-2 is inactive. Accordingly, it can be seen that SHP-1 or SHP-2 activity is essential for α-syn propagation Example 11. Effect of SHP-1 on Intracellular Aggregation of α-Syn At present, it is suggested that changes of monomeric α-syn into aggregates may be a main cause of Parkinson's disease, and therefore, it was examined whether overexpressed monomeric A53Tα-syn affects the changes of monomeric A53Tα-syn into aggregates when monomeric A53Tα-syn is overexpressed in SHSY5Y cells.

First, eGPF-tagged A53Tα-syn-overexpressed SHSY5Y cell line was prepared using lentivirus, and the prepared eGPP-tagged A53Tα-syn-overexpressed SHSY5Y cell line and α-syn-overexpressed SHSY5Y cell line were mixed, followed by co-culture. Further, A53Tα-syn-overexpressed SHSY5Y cell line and α-syn-overexpressed SHSY5Y cell line were mixed, followed by co-culture. At 5 days after the co-culture, intracellular distribution of eGFP-tagged A53Tα-syn was observed under confocal microscopy.

Figure 14A:
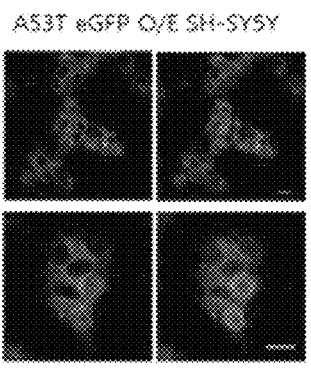
FIGS. 14A-14C are images showing whether the SHP-1/2 inhibitor, NSC87877 exhibits inhibitory effect during changes of monomeric α-syn to aggregates. eGPF-tagged A53T α-syn-overexpressed SHSY5Y is shown.
Figure 14B:
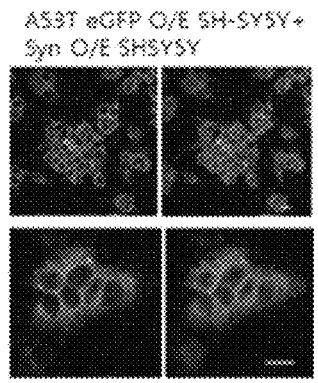

As a result, eGFP distribution in eGFP-tagged A53Tα-syn-overexpressed cells showed aggregation in the cells (FIG. 14B). In contrast, when only eGFP-tagged A53Tα-syn-overexpressed SHSY5Y cells were cultured, eGFP distribution in the cells showed less aggregation, compared to that of co-culture (FIG. 14A).

In this regard, the SHP-1/2 inhibitor, NSC87877 was treated and A53Tα-syn-overexpressed SHSY5Y cell line and α-syn-overexpressed SHSY5Y cell line were mixed, followed by co-culture. At 5 days after NSC 87877 treatment and co-culture, intracellular distribution of eGFP-tagged A53Tα-syn was observed under confocal microscopy.

Figure 14C:
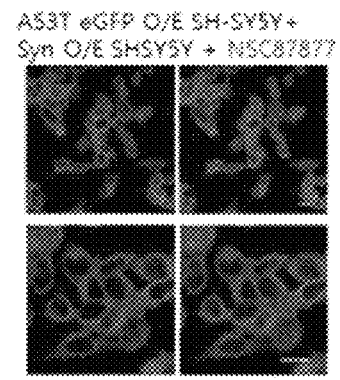

As a result, eGFP distribution in eGFP-tagged A53Tα-syn-overexpressed cells showed no aggregation in the cells (FIG. 14C).

Taken together, the results of Example 11 suggest that SHP-1 activation is essential for α-syn aggregation.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

An agent capable of suppressing expression or activity of SHP-1/-2 or FcγRIIB according to the present invention inhibits signal transduction caused by propagation of α-synuclein (α-Syn) to neighboring cells, thereby reducing cytotoxicity of α-synuclein to neighboring cells and thus being usefully applied to a therapeutic agent for neurodegenerative diseases.

Furthermore, the agent capable of suppressing expression or activity of SHP-1/-2 or FcγRIIB according to the present invention may be an important clue to elucidate the pathogenesis of neurodegenerative diseases, and therefore, contributes to fundamental cure, thereby overcoming neurodegenerative diseases.

What is claimed is:

1. A method of treating a neurodegenerative disease selected from the group consisting of Parkinson's disease, dementia with Lewy bodies, and multiple system atrophy, comprising administering a pharmaceutically effective amount of an agent capable of suppressing expression or activity of SHP-1/-2 (Src homology region 2 domain-containing phosphatase-1/-2) or FcγRIIB (IgG Fc receptor II-B) to a subject having the neurodegenerative disease, wherein the agent capable of suppressing expression of SHP-1/-2 or FcγRIIB is selected from the group consisting of miRNA, siRNA, shRNA, antisense oligonucleotide, and a combination thereof capable of specifically binding to mRNA of SHP-1/-2 or FcγRIIB, and wherein the agent capable of suppressing activity of SHP-1/-2 or FcγRIIB is selected from the group consisting of an antibody, an aptamer, an antagonist, and a combination thereof capable of specifically binding to a protein of SHP-1/-2 or FcγRIIB.

* * * * *